United States Patent [19]
Glazer et al.

[11] Patent Number: 6,150,107
[45] Date of Patent: Nov. 21, 2000

[54] METHODS OF SEQUENCING AND DETECTION USING ENERGY TRANSFER LABELS WITH CYANINE DYES AS DONOR CHROMOPHORES

[75] Inventors: Alexander N. Glazer, Orinda; Richard A. Mathies, Moraga; Su-Chun Hung, Richmond; Jingyue Ju, Redwood City, all of Calif.

[73] Assignee: The Regents of the University of California, Oakland, Calif.

[21] Appl. No.: 09/164,800

[22] Filed: Oct. 1, 1998

Related U.S. Application Data

[62] Division of application No. 08/726,178, Oct. 4, 1996, Pat. No. 5,853,992.

[51] Int. Cl.[7] .............................. C12Q 1/68; C12P 19/34; C07H 19/00; C07H 19/04; C07H 21/04
[52] U.S. Cl. .......................... 435/6; 435/91.1; 435/91.2; 536/22.1; 536/23.1; 536/24.3; 536/25.32; 536/25.3; 536/26.6
[58] Field of Search .............................. 435/6, 91.1, 91.2; 536/22.1, 23.1, 24.3, 25.3, 25.32, 26.6

[56] References Cited

U.S. PATENT DOCUMENTS 5,723,591   3/1998   Livak et al. ........................... 536/22.1

OTHER PUBLICATIONS

Livak et al. "Oligonucleotides with fluorescent dyes at opposite ends provide a quenched probe system useful for detecting PCR product and nucleic acid hybridization" PCR Methods and Applications, pp. 357–362, 1995.

*Primary Examiner*—Jezia Riley
*Attorney, Agent, or Firm*—Townsend and Townsend and Crew LLP

[57] ABSTRACT

Cyanine dyes are used as the donor fluorophore in energy transfer labels in which light energy is absorbed by a donor fluorophore and transferred to an acceptor fluorophore which responds to the transfer by emitting fluorescent light for detection. The cyanine dyes impart an unusually high sensitivity to the labels thereby improving their usefulness in a wide variety of biochemical procedures, particularly nucleic acid sequencing, nucleic acid fragment sizing, and related procedures.

28 Claims, 14 Drawing Sheets

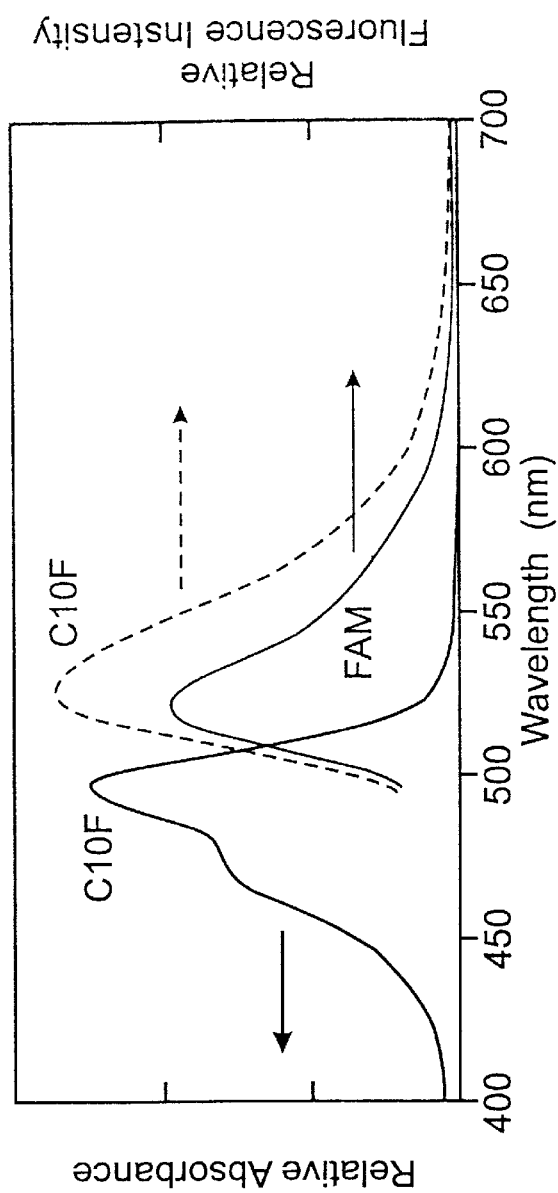
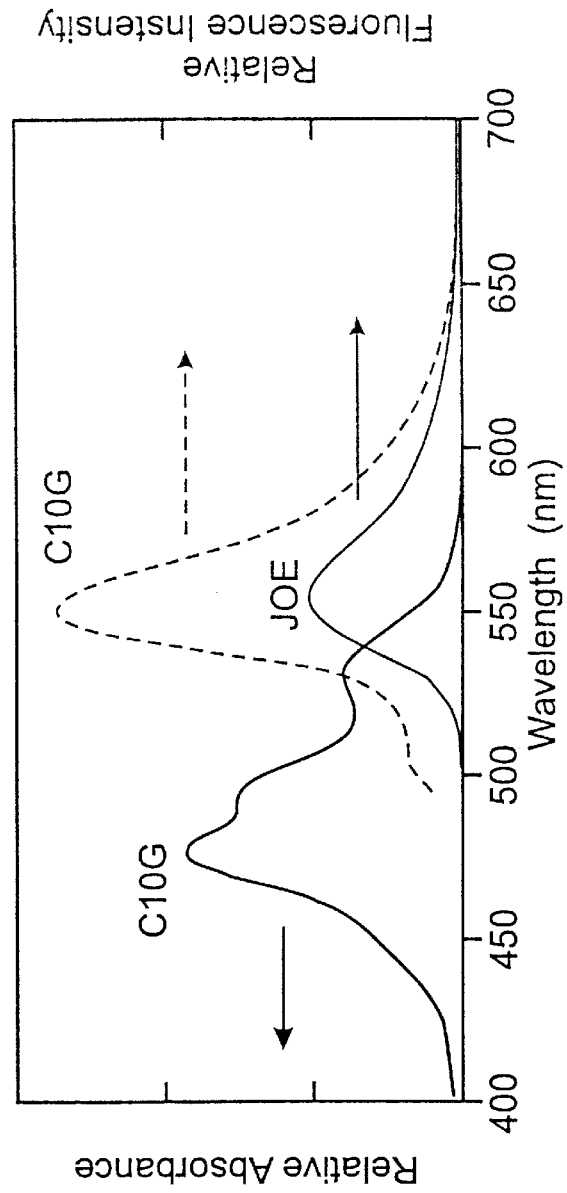
Fig. 3a
Fig. 3b

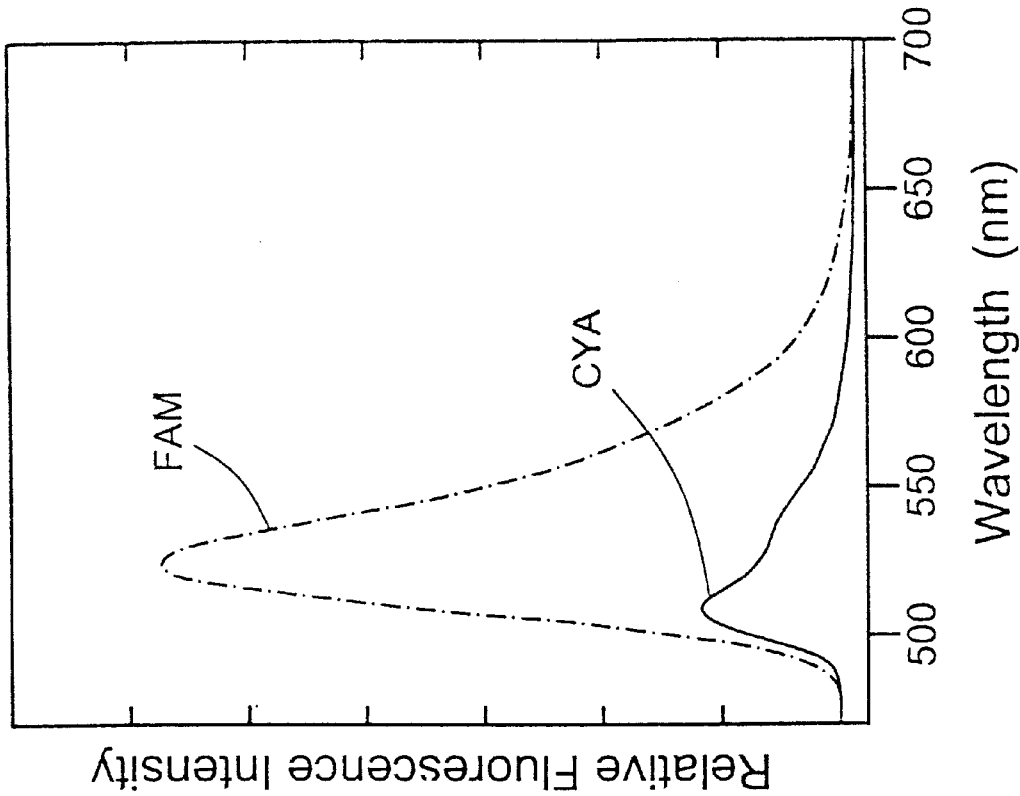
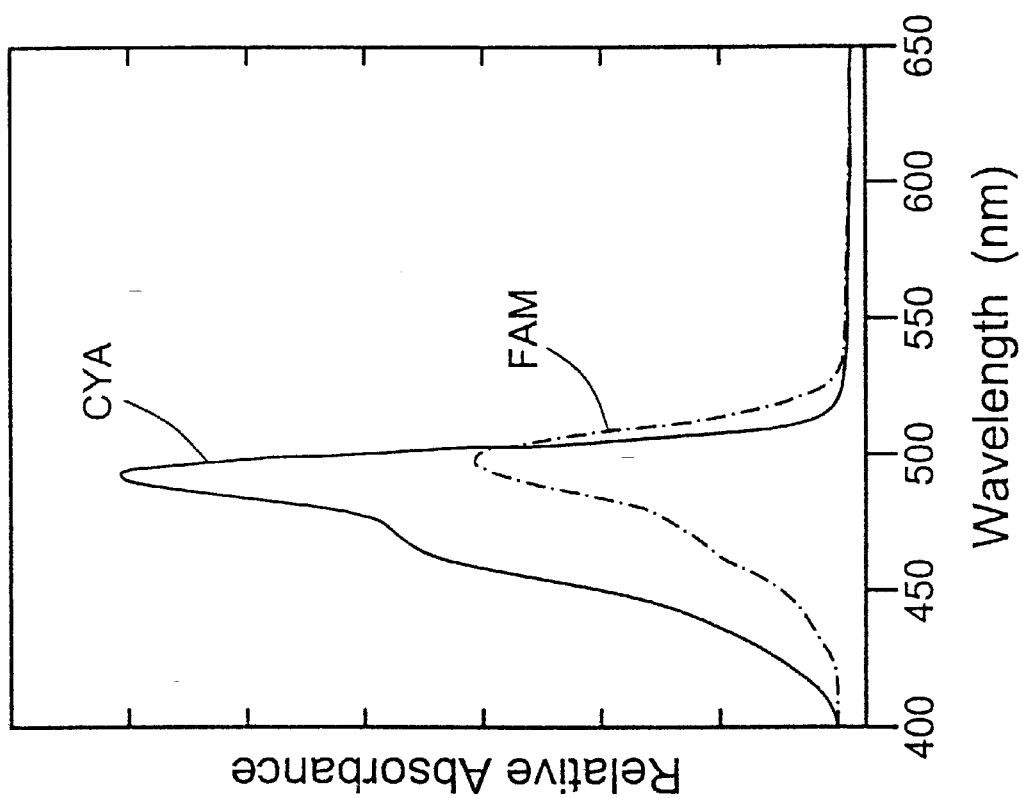
Fig. 5b
Fig. 5a

METHODS OF SEQUENCING AND DETECTION USING ENERGY TRANSFER LABELS WITH CYANINE DYES AS DONOR CHROMOPHORES

This application is a division of and claims the benefit of U.S. application Ser. No. 08/726,178, filed Oct. 4, 1996, U.S. Pat. No. 5,853,992 the disclosure of which is incorporated herein by reference.

GOVERNMENT RIGHTS

This invention was made with federal support from the Department of Energy, contract number DE-FG-91ER61125. The United States Government has certain rights in this invention.

BACKGROUND OF THE INVENTION

1. Field of the Invention

This invention resides in the field of energy transfer fluorescent labels.

2. Description of the Prior Art

Energy transfer between pairs of covalently linked fluorescent dyes is well known. The advantage of energy transfer is that the combined dyes produce a larger Stokes shift than either of the individual dyes, and this enhances each of the various procedures in which these covalently linked dyes are used as fluorescent labels by producing a clearer and more accurate readout. Included among these procedures are DNA sequencing, gene mapping studies and other nucleic acid fragment analyses, but the technology applies in general to any procedure in which a species of interest, or several distinct species, are labeled for purposes of detection, identification, or separation.

A recent development in the use of energy transfer dye pairs is the use of sets of energy transfer labels were each member of the set has a common donor fluorophore while the acceptor fluorophore differs from one member to the next within the set. Sets of this type are useful in the multiplexing of samples to separate, identify and detect two or more components simultaneously in a single procedure. One procedure in which these sets of labels are particularly useful is the Sanger dideoxy chain-termination method of DNA sequencing, but sets of this type are generally useful in any procedure where fluorescent labels are used to differentiate between components. By virtue of the common donor fluorophore, all labels in the set are irradiated at a single wavelength while fluorescent emissions are detected at distinct wavelengths that permit differentiation between the components. These sets and their uses are disclosed in International Patent Application Publication No. WO 95/21266, published Aug. 10, 1995 (Regents of the University of California, Mathies et al., and Wang, Y., et al., *Anal. Chem.* 67:1997–1203 (1995).

Selection of the particular donor and acceptor fluorophores to be used in synthesizing the labels and compiling the various members of a set is done with certain considerations. Included among these considerations are the wavelengths of the lasers available for irradiation, and the extinction coefficients, quantum yields, emission spectra, and photostability of the dyes. Unfortunately, donor/acceptor pairs used heretofore are not optimal in all of these properties, and this limits the sensitivity of the labels and their range of use. The best donor/acceptor pairs would be those in which the donor has superior photostability and a high extinction coefficient at the wavelength of available lasers, and in which the rate of energy transfer from the excited donor to the acceptor well exceeds the rates of the other processes that compete for the excited state of the donor, i.e., the natural fluorescence rate of the donor as well as the various radiationless processes that deplete the excited state of the donors.

SUMMARY OF THE INVENTION

It has now been discovered that a class of dyes, the cyanine dyes, not heretofore used as donors in energy transfer labels can indeed be used for this purpose, and when thus used, impart an unusually high sensitivity to the labels. As donor dyes in the present invention, these dyes are useful in combination with a wide variety of acceptor fluorophores to result in fluorescence emission intensities that are significantly higher than those obtained from energy transfer pairs formed from other donor and acceptor fluorophores. Use of these donor dyes improves the performance and usefulness of individual energy transfer labels as well as the performance and usefulness of sets of two or more labels of different emission spectra used in combination. The invention is therefore applicable to fluorescence labeling in general, as well as to the various processes in which fluorescence labeling is used. Energy transfer dye pairs containing these fluorophores are thus useful as labeled probes for identification and detection of nucleic acid fragments, and as labeled primers for nucleic acid sequencing.

BRIEF DESCRIPTION OF THE DRAWINGS

FIGS. 3a through 3d show the absorption and fluorescence emission spectra of four energy transfer labels in accordance with this invention, comparing them in each case with the emission spectra of the acceptor fluorophores alone. Each of the labels has the same donor fluorophore. The acceptor fluorophore in FIG. 3a is FAM; the acceptor fluorophore in FIG. 3b is R6G (compared with JOE rather than R6G alone); the acceptor fluorophore in FIG. 3c is TAMRA; and the acceptor fluorophore in FIG. 3d is ROX. In each case, the absorption spectrum of the label is the thick continuous line, the emission spectrum of the label is the dashed line, and the emission spectrum of the acceptor fluorophore alone is the thin continuous line.

FIG. 5a compares the absorbance spectrum of a donor fluorophore within the present invention with that of a donor fluorophore of the prior art. FIG. 5b compares the emission spectra of teh same two donor fluorophores.

DETAILED DESCRIPTION OF THE INVENTION AND PREFERRED EMBODIMENTS

Figure 1:
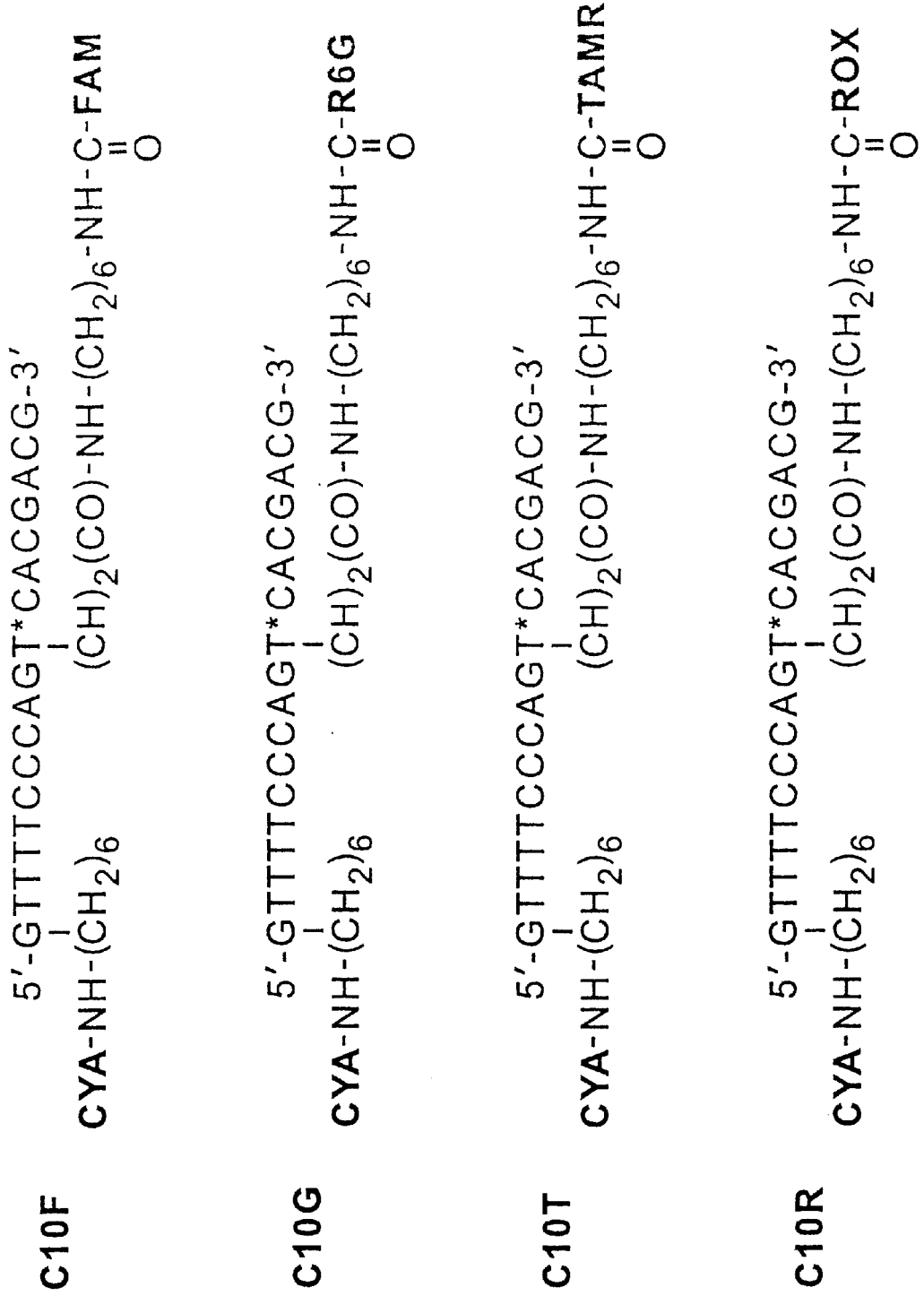
FIG. 1 depicts the structures of four energy transfer primers in according with this invention.

Cyanine dyes useful in this invention as donor fluorophores are those having a quantum yield within the range of about 0.01 to about 0.25. A preferred range for the quantum yield is from about 0.05 to about 0.15. Preferred cyanine dyes also have a molar extinction coefficient of greater than 60,000 $M^{-1}$ $cm^{-1}$, and a preferred range for the molar extinction coefficient is from about 100,000 $M^{-1}$ $cm^{-1}$ to about 250,000 $M^{-1}$ $cm^{-1}$. Further characteristics of preferred cyanine dyes are their absorption maxima, whose preferred range is from about 400 nm to about 900 nm, while the most preferred are those with absorption maxima ranging from about 480 nm to about 550 nm.

Particularly preferred cyanine dyes are those that, when bonded to the backbone, have the formula

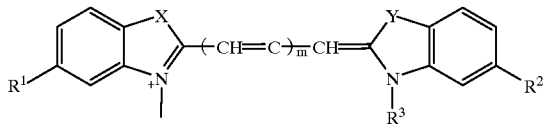

In this formula:

X is O or S;

Y is O or S;

$R^1$ is either H, halo, or $C_1$–$C_6$ alkyl;

$R^2$ is either H, halo, or $C_1$–$C_6$ alkyl;

$R^3$ is $C_1$–$C_6$ alkyl; and m is zero to 3.

Within this formula, certain embodiments are preferred. Preferred X and Y, for example, are O. Preferred groups for $R^1$ are H and $C_1$–$C_3$ alkyl, with H and methyl more preferred, and methyl the most preferred. Similarly, preferred groups for $R^2$ are H and $C_1$–$C_3$ alkyl, with H and methyl more preferred, and methyl the most preferred. For $R^3$, preferred groups are $C_1$–$C_3$ alkyl, with ethyl as the most preferred. Preferred values for m are 1, 2, and 3, with 1 the most preferred. Specific cyanine dyes of particular interest are 3-(ε-carboxypenyl)-3'-ethyl-5,5'-dimethyloxacarbocyanine and 3-(ε-carboxypentyl)-3"-ethyloxacarbocyanine, and of these the most preferred is 3-(ε-carboxypentyl)-3'-ethyl-5,5'-dimethyloxacarbocyanine.

When two or more different energy pairs or labels are used as a set for simultaneous excitation and detection of distinct components in a mixture, the cyanine donor fluorophores can be the same or different, but if different are preferably selected such that all cyanine dyes are efficiently excited at a common wavelength, preferably a single light source of narrow bandwidth, and particularly a laser source. The absorption maxima of the cyanine dyes are preferably within about 20 nm of each other, more preferably within about 10 nm, and still more preferably within about 5 nm. In the most preferred embodiments, the same cyanine dye will be used as the donor fluorophore for each pair or label.

The acceptor fluorophore will be selected on the basis of its ability to receive energy from the donor fluorophore by energy transfer and to emit light energy from the energy thus received. The acceptor fluorophores will generally by dyes other than the cyanine dyes used as donor fluorophores, since the acceptor fluorophores will preferably have quantum yields of about 0.3 or greater, and more preferably within the range of about 0.4 to about 0.9. In terms of their molar extinction coefficients, preferred acceptor fluorophores are those whose value is 30,000 $M^{-1}$ $cm^{-1}$ or higher, and more preferably within the range of about 40,000 to about 250,000 $M^{-1}$ $cm^{-1}$. The emission maxima for preferred acceptor fluorophores are at wavelengths in the range of about 450 nm to about 1,000 nm, and most preferably within the range of about 500 nm to about 700 nm.

Any of a wide variety of fluorescent dyes can be used as the acceptor fluorophore. Examples of types of fluorescent dyes are xanthene dyes, cyanine dyes, coumarins, benzimide dyes, phenanthridine dyes, ethidium dyes, acridine dyes, carbazole dyes, phenoxazine dyes, pophyrin dyes, and quinoline dyes. Subclasses of xanthene dyes are fluoresceins and rhodamines. An example of a coumarin is umbelliferone. An example of a benzimide dye is Hoechst 33258. An example of a phenanthridine dye is Texas Red. Xanthene dyes, and particularly fluorescein and rhodamine dyes, are of particular interest. Specific examples are 6-carboxyfluorescein (commonly known by the abbreviations FAM and F), 6-carboxy-4',5'-dichloro-2',7'-dimethoxyfluorescein (JOE or J), N,N,N',N'-tetramethyl-6-carboxyrhodamine (TAMRA or T), 6-carboxy-X-rhodamine (ROX or R), 5-carboxyrhodamine-6G (R6G[5] or G[5]), 6-carboxyrhodamine-6G (R6G[6] or G[5]), and rhodamine 110.

When two or more different energy pairs or labels are used as a set, each will contain a different acceptor fluorophore, each acceptor fluorophore emitting light that is detectably different from the other acceptor fluorophores in the set, thereby enabling the user to distinguish between the various labels in the set. In preferred embodiments of the usage of a set of labels, the individual labels in the set will emit at emission maxima separated by at least 10 nm, more preferably at least 15 nm, and most preferably at least 20 nm.

In addition to those embodiments in which the energy transfer relationship passes directly from the cyanine dye donor fluorophore to the acceptor fluorophore whose emitted energy is detected, this invention also contemplates energy transfer combinations in which energy is transferred from the cyanine dye donor fluorophore to two or more fluorophores in succession in a cascading manner, with emission detected from the final fluorophore in the cascade. Thus, labels of the present invention can include intervening fluorophores that will receive energy from the donor fluorophore and pass the energy thus received to further fluorophore(s) until it reaches the fluorophore from which fluorescence is emitted and detected. These combinations of three or more fluorophores in a single label offer the potential of an extended Stokes shift, i.e., a greater difference between the wavelength at which absorption occurs and the wavelength at which emission is detected. For example, excitation in the visible range with emission in the infra-red range, for example below 1,000 nm or preferably below 900 nm, can be obtained with the extended Stokes shift obtained by using three or more fluorophores. Detection in the infra-red range has the advantage that it is not subject to interference from Raman or Rayleigh scattering resulting from the excitation light.

Regardless of the number of fluorophores present on a single label, the fluorophores will be joined by a backbone or supporting structure that establishes the distance between fluorophores between which energy is transferred. The transfer of light energy between fluorophores varies as $1/R^6$, i.e., as the inverse of the sixth power of the R, where R is the distance between the two fluorophores. With this relationship as a guide, and the need to avoid self-quenching resulting from too small a spacing between adjacent fluorophores, the distance used between fluorophores can vary considerably. In general, the distance providing the most efficient energy transfer in accordance with the well-known Förster mechanism will be the preferred distance. The distance that provides the greatest efficiency for any particular label can further vary with the particular molecular structure of the backbone.

A variety of molecular structures can be used as the backbone. Examples of various classes of backbone structures are (a) nucleic acids, including both RNA and DNA, (b) modified nucleic acids, for example those where oxygen atoms are replaced by sulfur, carbon, or nitrogen atoms, and those where phosphate groups are replaced by sulfate groups, carboxylate group, or N-(2-aminoethyl)glycine, (c) polypeptides, (d) polysaccharides, and (e) groups that can be joined in stepwise manner, examples of which are di-functional groups such as haloamines.

Polymeric backbones are preferred. For many applications, a class of particular interest as the backbone is that of nucleic acids or oligonucleotides. The bases within the oligonucleotides include those that are naturally occurring as well synthetic bases, plus bases that have been modified to facilitate the attachment of the fluorophores; naturally occurring bases (including modified analogues) are currently of greatest interest. Oligonucleotide backbones contemplated in this invention are polymerized chains of monomeric units selected form purine and pyrimidine mononucleotides, hybridizing analogues of these mononucleotides, and all other structures listed in (a) and (b) above. Within this class, DNA and RNA are particularly preferred. The length of the oligonucleotide can vary considerably and is not critical to this invention. In most cases, best results will be obtained with oligonucleotides of 5 to 30, preferably 5 to 20, nucleotides in length. Applying the above condsiderations regarding the spacing of fluorophores on the backbone, the donor and acceptor fluorophores, or adjacent fluorophores in a fluorophore cascade of three or more, are preferably bonded to appropriately modified nucleotides that are separated by 1 to 29 intervening nucleotides, more preferably 1 to 15 intervening nucleotides, and most preferably 4 to 12 intervening nucleotides.

In addition to the energy transfer effect, the spacing between adjacent fluorophores will affect the mobility of the label, which will be of importance in separation processes where sets of labels are used for the separation and identification of two or more components in a mixture. The separation of the mixtures into components in these processes is based on the differences in the mobilities (for example, in electrophoretic separations) of these components. In these situations, it is preferred that the labels themselves do not contribute to or otherwise affect the mobility differences of the mixture components that the labels are attached to. It is thus preferred that the labels themselves, when unattached to any other species, have identical mobilities or that any differences in mobility among the labels be insignificant compared to the species being labeled. Differences in mobility between the labels themselves can be eliminated by varying the distances between the fluorophores, and this can be done while still achieving effective energy transfer. In general, the relationship between spacing and mobility is not linear, and best results are achieved by determining the effect of spacing on mobility in an empirical manner for any given label. Mobilities of the labels themselves are readily determined by performing the separation process on the labels alone. Alternatively, mobilities can be determined by first binding the labels to a common molecule that is relevant to the separation that will ultimately be performed, such as an oligonucleotide of the appropriate size, and then performing the separation process on the bound labels.

For embodiments of the invention where individual labels contain three or more fluorophores in energy-transfer relationship rather than a pair, the added fluorophores will also affect the mobility of the labels. It is therefore preferable when sets of different labels are used that each label within the set have the same number of fluorophores.

When it is necessary to control mobilities in set of labels by control of the spacing or any other technique, it is preferred that the mobilities within a set of labels be controlled to within about 20% of each other, more preferably within about 10% of each other, and most preferably within about 5% of each other.

Regardless of the particular backbone structure, the fluorophores can be attached by covalent means, notably by functionalization of a selected backbone component residing at the desired location along the backbone. The fluorophore can be attached either to the backbone component prior to its incorporation into the backbone or after the backbone has been formed.

The molecular weights of the labels (i.e., the fluorophores plus the backbone through which they are linked) will generally be at least about 250 Dal and not more than about 20,000 Dal, although usually not more than about 10,000 Dal. The molecular weight of each fluorophore will generally be in the range of about 250 to about 1,000 Dal, and the molecular weights of donor and acceptor fluorophores will usually not differ by more than about 30%. The donor and acceptor can be attached to the backbone at internal locations on the backbone, either one can be bound at a terminal position on the backbone, or both can be bound at terminal positions. In embodiments where the backbone is an oligonucleotide, the preferred site of attachment of one fluorophore is at the 5' terminal unit of the oligonucleotide. This can be either the donor or the acceptor, although in certain cases the donor is preferred.

This invention is particularly useful in processes involving nucleic acid chains, examples of such processes being DNA or RNA sequencing, the polymerase chain reaction (PCR), fragment sizing, and other procedures in which primers are employed for nucleic acid extension or ligation and in which distinctions must be made between various fragments. To apply this invention to the Sanger dideoxynucleotide sequencing technique, for example, universal primers can be employed with a set of different energy transfer labels, all having a cyanine dye as the donor fluorophore, with a different label for each of the different dideoxynucleotides. The method can be performed by hybridizing an oligonucleotide primer to the fragment, copying the fragment with a DNA polymerase in separate reaction vessels, each vessel containing dNTPs, one of a set of distinct energy transfer primers of this invention, and one of a set of dideoxynucleotides, to generate the single stranded DNA sequencing fragments. The resulting mixtures from each reaction vessel are then separated in individual lanes on a gel, and the sequence is determined from the relative locations of bands on the gel.

A large number of nucleotides, already functionalized, are available for use in the synthesis of a polynucleotide. In synthesizing labels having nucleic acids as backbones, one can establish specific sites for the attachment of the fluorophores. Synthesizers well known among those skilled in polynucleotide synthesis can be employed and used in conventional procedures to achieve a desired sequence including either the fluorophores or sites for selective fluorophore attachment at selected locations along the chain.

In polymerase chain reactions where different primers are used, each of the primers can be labeled in accordance with this invention, permitting detection of the presence of the target sequence complementary to each of the different primers. Double or single stranded nucleic acid fragments can be identified and detected in this manner, by labeling each fragment by means of a polymerase chain reaction employing energy transfer primers of this invention, separating the labeled fragments according to their mobilities, and detecting the fragments by irradiating the labels. Identification and detection of nucleic acid fragments in a mixture by hybridization is achieved by hybridizing different fragments in the mixture to different energy transfer probes of this invention, separating the hybridized fragments, and detecting them by irradiation of the probes. Procedures depending on fragment labeling by ligation are performed in an analogous manner.

This invention is also useful in many other applications, an example of which is identifying lectins by use of different polysaccharides. A further example is the rapid sizing of alleles, as exemplified by short tandem repeat (STR) alleles, or other sequences where a small number of base pair differences are to be detected, such as a difference of a single base pair. By using labels in accordance with this invention in conjunction with capillary electrophoresis, particularly capillary array electrophoresis, and employing an intercalating agent in the buffer, separations differing by one base can be achieved. This method can be used with dsDNA, particularly dsDNA obtained using the polymerase chain reaction or the ligase chain reaction, where the labels of this invention are used as primers. The labels can serve as one or both of the primers used for the amplification, and the fluorophore pairs can be the same or different, depending on the needs of the separation. The intercalating agents can be either fluorescent or non-fluorescent, and can include such examples as thiazole orange, 9-aminoacridine, ethidium bromide. Non-fluorescent intercalating agents are preferred. Concentrations will generally be within the range of 0.1 $\mu$M to 1.0 $\mu$M. Capillary electrophoresis can be conducted in the conventional manner, using a polyacrylamide wall coating and, for example, hydroxyethylcellulose at from about 0.5% to 1% in an appropriate running buffer. Voltages may vary from about 50 to about 150 V/cm or greater. The amount of DNA will generally be in the range of about 1 pg/$\mu$L to 1 ng/$\mu$L, although greater or lesser amounts can be used. Fragment analyses of single strand DNA can be performed in an analogous manner, using linear polyacrylamide or the like in capillary electrophoresis. For these procedures and others involving nucleic acid hybridization, the nucleotide sequence of the backbone structure that separates the fluorophores in the labels of this invention can include the nucleotides that hybridize to the complementary sequence, or the hybridizing nucleotides can lie outside both fluorophores and thus be separated from the nucleotides that separate the fluorophores.

Linkage of the fluorophores to the backbone is achieved by conventional covalent binding. Linking arms suitable for this type of purpose are well known in the art, and include a wide variety of structures. Examples are aliphatic groups, alicyclic groups, aromatic groups, heterocyclic groups, and combinations of these structures, as well as aliphatic groups interrupted by an ester group, an amide group, an amino groups, a C=O group, a C=S group, a C(O)—O group, a C(S)—O group, a C(O)—S group, a C(S)—S group, an oxygen atom, and a sulfur atom. In the case of nucleic acid backbones, linkage is preferably achieved by use of a convenient linking arm usually consisting of from about 2 to about 20, and preferably from about 4 to about 16, atoms. A preferred linking group structure is an amide-containing chain bonding directly to the heterocyclic nitrogen atom on the cyanine dye, particularly one of the formula

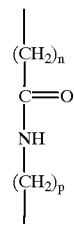

where n is 1 to 10, and p is 1 to 10. Preferred values for n in this formula are 1 to 6, more preferred are 4 to 6, and a value of 5 is particularly preferred. Preferred values for p in this formula are 2 to 8, more preferred are 3 to 6, and a value of 6 is particularly preferred. For nucleic acid chains, a linking group of the above formula preferably serves as the linkage between the heterocyclic nitrogen in the cyanine dye and the phosphate group of the nucleotide.

In hybridization applications, the entire nucleic acid sequence of the backbone can be complementary to the 5' primer sequence, or only to the 3' portion of the sequence, or to any portion within the target sequence. Usually, there will be at least about 4 nucleotides, more usually at least about 5 nucleotides that are complementary to the sequence to be copied. For PCR, the primers are combined with a mixture of the sequence to be amplified, Taq polymerase, and dNTPs. After amplification, the DNA can be isolated and transferred to a gel or capillary for separation.

The following examples are offered for purposes of illustration and are not intended to limit the scope of the invention.

Materials and Analytical Methods

2-Methylbenzoxazole, 2,5-dimethylbenzoxazole, iodoethane, iodoacetic acid, 3-iodopropionic acid, 6-bromohexanoic acid, acetic anhydride, 1,2-dichlorobenzene, N,N'-diphenylformamidine, and N,N'-disuccinimidyl carbonate were purchased from Aldrich Chemical Co. (Milwaukee, Wis., USA) and used without further purification. All other solvents were purchased from Fisher Scientific (Pittsburgh, Pa., USA); absolute ethanol was used as purchased. Pyridine, dimethylformamide and triethylamine were stored over 4 Å molecular sieves for at least one day before use.

Chemicals used for the synthesis of oligonucleotides were purchased from Applied Biosystems Inc. (Foster City, Calif., USA) unless otherwise stated. Thermo Sequenase and other DNA sequencing reagents were obtained from Amersham Life Science Inc. (Cleveland, Ohio, USA).

Reactions were monitored by thin layer chromatography (TLC) (silica gel GHLF Uniplates, Analtech Inc., Newark, Del., USA) under short and long wavelength UV light. Column chromatography was performed on 220–440 mesh silica gel 60 from Fluka (Ronkonkoma, N.Y., USA). Purified products which gave single spots on TLC were characterized by their $^1$H NMR spectra and by their UV-vis absorption spectra.

Proton nuclear magnetic resonance spectra were recorded on a Bruker AMX spectrometer at 300 MHz. Unless otherwise specified, samples were dissolved in 5% $CD_3OD$/$CDCl_3$ with tetramethylsilane (TMS) as an internal reference. NMR signals are described by use of s for singlet, d for doublet, t for triplet, q for quarter, and m for multiplet and the chemical shifts ($\delta$) are reported in ppm.

Absorption spectra were measured on a Perkin-Elmer Lambda 6 UV-visible spectrophotometer. Fluorescence emission spectra were taken on a Perkin-Elmer model MPF 44B spectrofluorimeter. Samples were prepared at a concentration of $1 \times 10^{-5}$ M in methanol or 1×TBE buffer (89 mM Tris/89 mM boric acid/2 mM ethylenediamine tetraacetic acid (EDTA), pH 8.0) containing 7 M urea.

The symmetric cyanine dyes 3,3'-diethyloxacarbocyanine iodide (DOCCI) and 3,3'-diethyl-5,5'-dimethyloxacarbocyanine iodide were used as standards for the $^1$H NMR studies and the spectroscopic analyses. In the spectral data, MeOH designates methanol. AcOH designates acetic acid, and PhH designates benzene.

Synthesis of Cyanine Dye Donors

Quaternized nitrogen heterocycle derivatives 3-ethyl-2-methylbenzoxazolium iodide and 3-ethyl-2,5-dimethylbenzoxazolium iodide were synthesized by alkylation of 2-methylbenzoxazole and 2,5-dimethylbenzoxazole, respectively, with 5 equivalents of iodoethane, refluxing overnight under $N_2$. These reaction products were isolated as solids after precipitation with ethyl ether to give pure 3-ethyl-2-methylbenzoxazolium iodide (91%) and 3-ethyl-2,5-dimethylbenzoxazolium iodide (60%), respectively. The structure of 3-ethyl-2,5-dimethylbenzoxazolium iodide was verified by spectral data as follows: $^1$H NMR ($CDCl_3$) $\delta$ 1.70 (3H, t, J=7.5 Hz, $\beta$-$CH_3$), 2.59 (3H, s, 5-$CH_3$), 3.43 (3H, s, 2-$CH_3$), 4.83 (2H, q, J=7.5 Hz, $\alpha$-$CH_2$), 7.50 (1H, d, J=8.6 Hz, 6-H), 7.70 (1H, d, J=8.6 Hz, 7-H), 7.71 (1H, s, 4-H).

Similarly, four derivatives—3-($\epsilon$-carboxypentyl)-2-methylbenzoxazolium bromide, 3-($\epsilon$-carboxypentyl)-2,5-dimethylbenzoxazolium bromide, 3-($\beta$-carboxyethyl)-2,5-dimethylbenzoxazolium iodide, and 3-($\alpha$-carboxymethyl)-2,5-dimethylbenzoxazolium iodide—were formed by carboxyalkylation of 2-methylbenzoxazole and 2,5-dimethylbenzoxazole with two equivalents of iodoacetic acid, 3-iodopropionic acid, or 6-bromohexanoic acid in dry 1,2-dichlorobenzene (5 g of benzoxazole/20 mL of 1,2-dichlorobenzene) at 110–120° C. for 17 hours under $N_2$, followed by precipitation with $CH_2Cl_2$ to give the four derivatives in pure form in 45–55% yield. The structures of these four derivatives were verified as follows:

3-($\epsilon$-Carboxypentyl)-2-methylbenzoxazolium bromide: $^1$H NMR $\delta$ 1.46–1.54 (2H, m, $\gamma$-$CH_2$), 1.60–1.70 (2H, m, $\delta$-$CH_2$), 1.93–2.04 (2H, m, $\beta$-$CH_2$), 2.29 (2H, t, J=6.9 Hz, $\epsilon$-$CH_2$), 3.27 (3H, s, 2-$CH_3$), 4.67 (2H, t, J=7.5 Hz, $\alpha$-$CH_2$), 7.65–7.87 (4H, m, PhH).

3-($\epsilon$-Carboxypentyl)-2,5-dimethylbenzoxazolium bromide: $^1$H NMR $\delta$1.44–1.54 (2H, m, $\gamma$-$CH_2$), 1.61–1.71 (2H, m, $\delta$-$CH_2$), 1.92–2.03 (2H, m, $\beta$-$CH_2$), 2.30 (2H, t, J=6.9 Hz, $\epsilon$-$CH_2$), 2.55 (3H, s, 5-$CH_3$), 3.24 (3H, s, 2-$CH_3$), 4.63 (2H, t, J=7.5 Hz, $\alpha$-$CH_2$), 7.47 (1H, d, J=8.7 Hz, 6-H), 7.60 (1H, s, 4-H), 7.66 (1H, d, J=8.7 Hz, 7-H).

3-($\beta$-Carboxyethyl)-2,5-dimethylbenzoxazolium iodide: $^1$H NMR $\delta$ 2.47 (3H, s, 5-$CH_3$), 3.00 (2H, t, J=5.9 Hz, $\beta$-$CH_2$), 3.16 (3H, s, 2-$CH_3$), 4.73 (2H, t, J=5.9 Hz, $\alpha$-$CH_2$), 7.40 (1H, d, J=8.7 Hz, 6-H), 7.60 (1H, d, J=8.7 Hz, 7-H), 7.67 (1H, s, 4-H).

3-($\alpha$-Carboxymethyl)-2,5-dimethylbenzoxazolium iodide: $^1$H NMR $\delta$ 2.57 (3H, s, 5-$CH_3$), 3H, s, 2-$CH_3$), 5.45 (2H, s, $\alpha$-$CH_2$), 7.52 (1H, d, J=8.7 Hz, 6-H), 7.57 (1H, s, 4-H), 7.73 (1H, d, J=8.7 Hz, 7-H).

The compounds 3-ethyl-2-methylbenzoxazolium iodide or 3-ethyl-2,5-dimethylbenzoxazolium iodide were reacted with conjugated N,N'-diphenylformamidine in refluxing acetic anhydride yielding intermediate acetanilide derivatives 2-(2'-acetaniliodivinyl)-3-ethylbenzoxazolium iodide or 2-(2'-acetaniliodivinyl)-3-ethyl-5-methylbenzoxazolium iodide in 67–84% yield. The structure of the 2-(2'-acetanilidovinyl)-3-ethyl-5-methyl-benzoxazolium iodide thus produced as verified as follows: $^1$H NMR ($CDCl_3$) $\delta$ 1.41 (3H, t, J=7.4 Hz, $\beta$-$CH_3$), 2.10 (3H, s, aceto-$CH_3$), 2.54 (3H, s, 5-$CH_3$), 4.56 (2H, q, J=7.4 Hz, $\alpha$-$CH_2$), 5.46 (1H, d, J=13.7 Hz, bridge $\alpha$-H), 7.37–7.73 (8H, m, PhH), 9.25 (1H, d, J=13.7 Hz, bridge $\beta$-H).

Each of these intermediates was then coupled with one equivalent of the activated quaternary heterocycles prepared in the preceding paragraphs, in the presence of two equivalents of triethylamine in dry ethanol (heated to reflux for 30 minutes) to form the asymmetric (carboxyalkyl)cyanine dyes whose identities and spectral verification data are given below:

3($\epsilon$-Carboxypenyl)-3'-ethoxacarbocyanine: $^1$H NMR $\delta$ 1.38–1.48 (2H, m, $\gamma CH_2$), 1.41 (3H, t, J=7.3 Hz, $\beta$'-$CH_3$), 1.56–1.66 (2H, m, $\delta$-$CH_2$), 1.76–1.81 (2H, m, $\beta$-$CH_2$), 2.14 (2H, t, J=7.0 Hz, $\epsilon$-$CH_2$), 4.02 (2H, t, J=7.3 Hz, $\alpha$-$CH_2$), 4.10 (2H, q, J=7.3 Hz, $\alpha$'-$CH_2$), 5.85 (1H, d, J=13.3 Hz, bridge $\alpha$-H), 5.87 (1H, d, J=13.3 Hz, bridge $\alpha$'-H), 7.23–7.45 (8H, m, PhH), 8.41 (1H, t, J=13.3 Hz, bridge $\beta$-H); $\lambda_{max}^{Abs}$ (MeOH)=484 nm; $\lambda_{max}^{Em}$ (MeOH)=500 nm.

3-($\epsilon$-Carboxypenyl)-3'-ethyl-5,5'-dimethyloxacarbocyanine: $^1$H NMR ($CDCl_3$) $\delta$ 1.50 (3H, t, J=7.2 Hz, $\beta$'-$CH_3$), 1.53–1.63 (2H, m, $\gamma$-$CH_2$), 1.73–1.84 (2H, m, $\delta$-$CH_2$), 1.84–1.95 (2H, m, $\beta$-$CH_2$), 2.40 (2H, t, J=6.9 Hz, $\epsilon$-$CH_2$), 2.46 (3H, s, 5-$CH_3$), 2.47 (3H, s, 5'-$CH_3$), 4.17 (2H, t, J=7.1 Hz, $\alpha$-$CH_2$), 4.30 (2H, q, J=7.2 Hz, $\alpha$'-$CH_2$), 5.09 (1H, brs, $CO_2H$), 6.27 (1H, d, J=13.3 Hz, bridge $\alpha$-H), 6.38 (1H, d, J=13.3 Hz, bridge $\alpha$'-H), 7.06–7.13 (4H, m, 4-H, 4'-H, 6-H and 6'-H), 7.30–7.35 (2H, m, 7-H and 7'-H), 8.38 (1H, t, J=13.3 Hz, bridge $\beta$-H); $\lambda_{max}^{Abs}$ (MeOH)=490 nm; $\lambda_{max}^{Em}$ (MeOH)=504 nm.

3-($\beta$-Carboxyethyl)-3'-ethyl-5,5'-dimethyloxacarbocyanine: $^1$H NMR $\delta$ 1.41 (3H, t, J=7.2 Hz, $\beta$'-$CH_3$), 2.40 (3H, s, 5'-$CH_3$), 2.41 (3H, s, 5-$CH_3$), 2.60 (2H, t, J=7.4 Hz, $\beta$-$CH_2$), 4.04 (2H, q, J=7.2 Hz, $\alpha$'-$CH_2$), 4.28 (2H, t, J=7.4 Hz, $\alpha$-$CH_2$), 5.76 (1H, d, J=13.3 Hz, bridge $\alpha$'-H), 6.01 (1H, d, J=13.3 Hz, bridge $\alpha$-H), 7.00–7.30 (6H, m, PhH), 8.35 (1H, t, J=13.3 Hz, bridge $\beta$-H); $\lambda_{max}^{Abs}$ (MeOH)=490 nm; $\lambda_{max}^{Em}$ (MeOH)=504 nm.

3-($\alpha$-Carboxymethyl)-3'-ethyl-5,5'-dimethyloxacarbocyanine: $^1$H NMR $\delta$ 1.41 (3H, t, J=7.3 Hz, $\beta$'-$CH_3$), 2.39 (3H, s, 5'-$CH_3$), 2.42 (3H, s, 5-$CH_3$), 4.06 (2H, q, J=7.3 Hz, $\alpha$'-$CH_2$), 4.55 (2H, s, $\alpha$-$CH_2$), 5.78 (1H, d, J=13.3 Hz, bridge $\alpha$'-H), 5.84 (1H, d, J=13.3 Hz, bridge $\alpha$-H), 7.00–7.30 (6H, m, PhH), 8.36 (1H, t, J=13.3 Hz, bridge $\beta$-H); $\lambda_{max}^{Abs}$ (MeOH)=490 nm; $\lambda_{max}^{Em}$ (MeOH)=503 nm.

These crude dyes were purified by flash column chromatography on silica gel, eluting with $CH_2Cl_2$:MeOH:AcOH (90:10:1, by volume) to give the dyes (90–97% yield) as red powders.

The symmetric cyanine dyes 3,3'-diethyloxacarbocyanine iodide (DOCCI) and 3,3'-diethyl-5,5'-dimethyloxacarbocyanine iodide, that were used as standards for $^1$H NMR studies and spectroscopic analyses, can be synthesized in quantitative yield by condensation of intermediates 3-ethyl-2,5-dimethylbenzoxazolium iodide and 2-(2'-acetanilidovinyl)-3-ethyl-5-methylbenzoxazolium iodide, or their analogs, following the procedure for the synthesis of asymmetric cyanine dyes. The structure of 3,3'-diethyl-5,5'-dimethyloxacarbocyanine iodide was verified as follows: $^1$H NMR ($CDCl_3$) δ 1.54 (6H, t, J=7.3 Hz, β-$CH_3$ and β'-$CH_3$), 2.49 (6H, s, 5-$CH_3$ and 5'-$CH_3$), 4.31 (4H, q, J=7.3 Hz, α-$CH_2$ and α'-$CH_2$), 6.78 (2H, d, J=13.2 Hz, bridge α- and α'-H), 7.07 (2H, s, 4-H and 4'-H), 7.11 (2H, d, J=8.3 Hz, 6-H and 6'-H), 7.33 (2H, d, J=8.3 Hz, 7-H and 7'-H), 8.44 (1H, J=13.2 Hz, bridge β-H); $\lambda_{max}^{Abs}$ (MeOH)=488 nm; $\lambda_{max}^{Em}$ (MeOH)=502 nm.

Synthesis of N-hydroxysuccinimide Esters of (Carboxyalkyl)cyanine Dyes

Active N-hydroxysuccinimide (NHS) esters of (carboxyalkyl)cyanine dyes were prepared by a modification of the method of Ogura, H., et al., *Tetrahedron Lett.* 49:4745–4746 (1979). In a typical procedure, two equivalents of anhydrous pyridine and 1.5 equivalents of N,N'-disuccinimidyl carbonate were added to a stirred solution of 3-(ε-carboxypentyl)-3'-ethyloxacarbocyanine of 3(ε-carboxypenyl)-3'-ethyl-5,5'-dimethyloxacarbocyanine in dry dimethylformamide (DMF) (100 mg of dye/2 mL of DMF) under $N_2$. The reaction mixture was stirred at 60° C. for 60 minutes. After evaporation of the solvent, the deep-red residue was purified by column chromatography (silica gel, $CH_2Cl_2$:$CH_3OH$, 95:5 by volume). Pure cyanine dye active esters were recrystallized from ethyl acetate to give nearly quantitative yields of the NHS ester of 3-(ε-carboxypentyl)-3'-ethyloxacarbocyanine and the NHS ester of 3-(ε-carboxypentyl)-3'-ethyl-5,5'-dimethyloxacarbocyanine as red powders. Structure verification was as follows:

NHS ester of 3-(ε-carboxypentyl)-3'-ethyloxacarbocyanine: $^1$H NMR ($CDCl_3$) δ 1.51 (3H, t, J=7.3 Hz, β'-$CH_3$), 1.59–1.69 (2H, m, γ-$CH_2$), 1.78–1.89 (2H, m, δ-$CH_2$), 1.92–2.00 (2H, m, β-$CH_2$), 2.62 (2H, t, J=7.1 Hz, ε-$CH_2$), 2.82 (4H, s, succinimido $CH_2CH_2$), 4.25 (2H, t, J=7.3 Hz, α-$CH_2$(, 4.31 (2H, q, J=7.3 Hz, α-'$CH_2$), 6.63 (1H, d, J=13.2 Hz, bridge α-H), 6.65 (1H, d, J=13.2 Hz, bridge α'-H), 7.26–7.49 (8H, m, PhH), 8.44 (1H, t, J=13.2 Hz, bridge β-H); $\lambda_{max}^{Abs}$ (MeOH)=484 nm; $\lambda_{max}^{Em}$ (MeOH)=502 nm.

NHS ester of 3-(ε-carboxypentyl)-3'-ethyl-5,5'-dimethyloxacarbocyanine: $^1$H NMR ($CDCl_3$) δ 1.53 (3H, t, J=7.2 Hz, β'-$CH_3$), 1.63–1.73 (2H, m, γ-$CH_2$), 1.82–2.02 (4H, m, β-$CH_2$ and δ-$CH_2$), 2.47 (6H, s, 5-$CH_3$ and 5'-$CH_3$), 2.67 (2H, t, J=7.1 Hz, ε-$CH_2$), 2.84 (4H, s, succinimido $CH_2CH_2$), 4.23 (2H, t, J=7.5 Hz, α-$CH_2$), 4.29 (2H, q, J=7.2 Hz, α'-$CH_2$), 6.74 (1H, d, J=13.2 Hz, bridge α-H), 6.75 (1H, d, J=13.2 Hz, bridge α'-H), 7.08–7.11 (4H, m, 4-H, 4'-H, 6-H and 6'-H), 7.30–7.34 (2H, m, 7-H and 7'-H), 8.42 (1H, t, J=13.2 Hz, bridge β-H), $\lambda_{max}^{Abs}$ (MeOH)=489 nm; $\lambda_{max}^{Em}$ (MeOH)=505 nm.

The structures of the various dyes, together with the wavelengths of their absorption and emission maxima are shown in the following table, where:

Dye No. 1 is 3,3'-diethyloxacarbocyanine iodide (DOCCI),

Dye No. 2 is 3,3'-diethyl-5,5'-dimethyloxacarbocyanine iodide,

Dye No. 3 is 3-(ε-carboxypentyl)-3'-ethyloxacarbocyanine,

Dye No. 4 is 3-(ε-carboxypentyl)-3'-ethyl-5,5'-dimethyloxacarbocyanine,

Dye No. 5 is 3-(β-carboxyethyl)-3'-ethyl-5,5'-dimethyloxacarbocyanine,

Dye No. 6 is 3-(α-carboxymethyl)-3'-ethyl-5,5'-dimethyloxacarbocyanine,

Dye No. 7 is the NHS ester of 3-(ε-carboxypentyl)-3'-ethyloxacarbocyanine, and

Dye No. 8 is the NHS ester of 3-(ε-carboxypentyl)-3'-ethyl-5,5'-dimethyloxacarbocyanine.

Structure and Spectral Properties Of Oxabarbocyanine Dyes

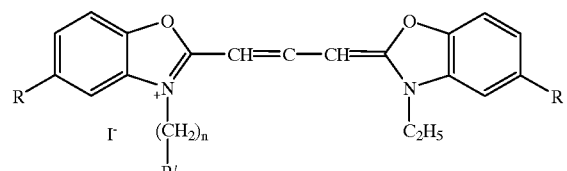

| Dye No. | R | R' | n | $\lambda_{max}^{Abs}$ (nm) | $\lambda_{max}^{Em}$ (nm) | Solvent |
|---|---|---|---|---|---|---|
| 1 | H | $CH_3$ | 1 | 483 | 500 | $CH_3OH$ |
| 2 | $CH_3$ | $CH_3$ | 1 | 488 | 502 | $CH_3OH$ |
|   |   |   |   | 486 | 502 | $H_2O$ |
| 3 | H | COOH | 5 | 484 | 500 | $CH_3OH$ |
|   |   |   |   | 485 | 504 | 1 × TBE, 7M urea |
| 4 | $CH_3$ | COOH | 5 | 490 | 504 | $CH_3OH$ |
|   |   |   |   | 491 | 508 | 1 × TBE, 7M urea |
| 5 | $CH_3$ | COOH | 2 | 490 | 504 | $CH_3OH$ |
|   |   |   |   | 491 | 508 | 1 × TBE, 7M urea |
| 6 | $CH_3$ | COOH | 1 | 490 | 503 | $CH_3OH$ |
|   |   |   |   | 491 | 507 | 1 × TBE, 7M urea |
| 7 | H | COOSu | 5 | 484 | 502 | $CH_3OH$ |
|   |   |   |   | 485 | 504 | 1 × TBE, 7M urea |
| 8 | $CH_3$ | COOSu | 5 | 489 | 505 | $CH_3OH$ |
|   |   |   |   | 491 | 508 | 1 × TBE, 7M urea |

"Su" denotes succinimidyl

Design and Synthesis of ET Primers

The structure of the 5'-end of each of the cyanine dye-labeled primers whose preparations are described below is shown in the following formula. In this formula, the cyanine dye is joined to the 5'-end nucleotide guanosine through an amide linking group, a portion of which is supplied by the structure of the starting dye. The remaining nucleotides are indicated by the words "Primer Sequences."

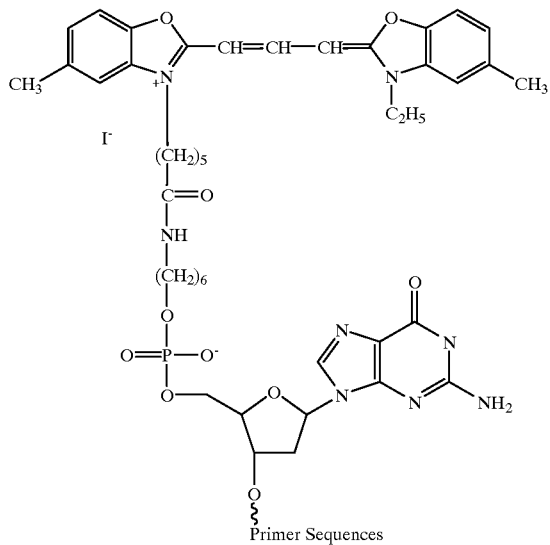

Primer Sequences

The primers used were M13 (−40) universal primers containing 18 nucleotides and two primary amine linker arms (protected by two different groups). The oligonucleotide sequence of each primer was 5'-GTTTTCCCAGT*CACGACG-3', synthesized by the phosphoramidite method on an Applied Biosystems 392 DNA synthesizer. The protected primary amine linker arm at the 5' end was introduced in the last step of the oligonucleotide synthesis using 6-(4-monomethoxytritylamino)hexyl-(2-cyanoethyl)-(N,N-diisopropyl)-phosphoramidite (5'-Amino-Modifier C6, Glen Research, Sterling, Va., USA). The symbol T* represents a modified thymidine (T*), characterized by a linker arm terminating in a primary amine, introduced by the use of 5'-dimethoxytrityl-5-[N-(trifluoroacetylaminohexyl)-3-acrylimido]-2'-deoxyuridine, 3'-[(2-cyanoethyl)-(N,N-diisopropyl)]-phosphoramidite (Amino-Modifier C6dT, Glen Research). Donor-acceptor fluorophore pairs were attached at nucleotides separated by 10 intervening bases, as described below.

The starting oligonucleotide was produced at the 5' end with a monomethoxytrityl (MMT) group, and bore the modified thymidine T* as described above. The synthesis was begun by coupling the acceptor dyes to the primary amino group on the T* in the presence of $Na_2CO_3/NaHCO_3$ at pH 9 in dimethyl sulfoxide (DMSO). The acceptor dyes used were 6-carboxyfluorescein (FAM), 6-carboxy-4',5'-dichloro-2',7'-dimethoxyfluorescein (JOE), N,N,N',N'-tetramethyl-6-carboxyrhodamine (TAMRA), 6-carboxy-X-rhodamine (ROX), 5-carboxyrhodamine-6G or 6-carboxyrhodamine-6G (R6G), and rhodamine 110. Coupling of the acceptor dyes was followed by the removal of the monomethoxytrityl (MMT) protecting group on the 5' end by treatment with trifluoroacetic acid, and then the donor dye 3-(ε-carboxypentyl)-3'-ethyl-5,5'-dimethyloxacarbocyanine (also referred to herein by the abbreviation CYA) was introduced at the 5' end of the oligomer, again in the presence of $Na_2CO_3/NaHCO_3$ at pH 9 in DMSO. The primers are named according to the convention D-N-A, where D is the donor, N is the number of bases between the donor and the acceptor, and A is the acceptor. The donor and acceptor in this convention are represented by single-letter symbols. For the cyanine dye 3-(ε-carboxypentyl)-3'-ethyl-5,5'-dimethyloxacarbocyanine (CYA), the single-letter symbol is C. The acceptor fluorophores are likewise designated by the single-letter symbols F for FAM, G for R6G, T for TAMRA, R for ROX, and $R^{110}$ for rhodamine 110.

Figure 2:
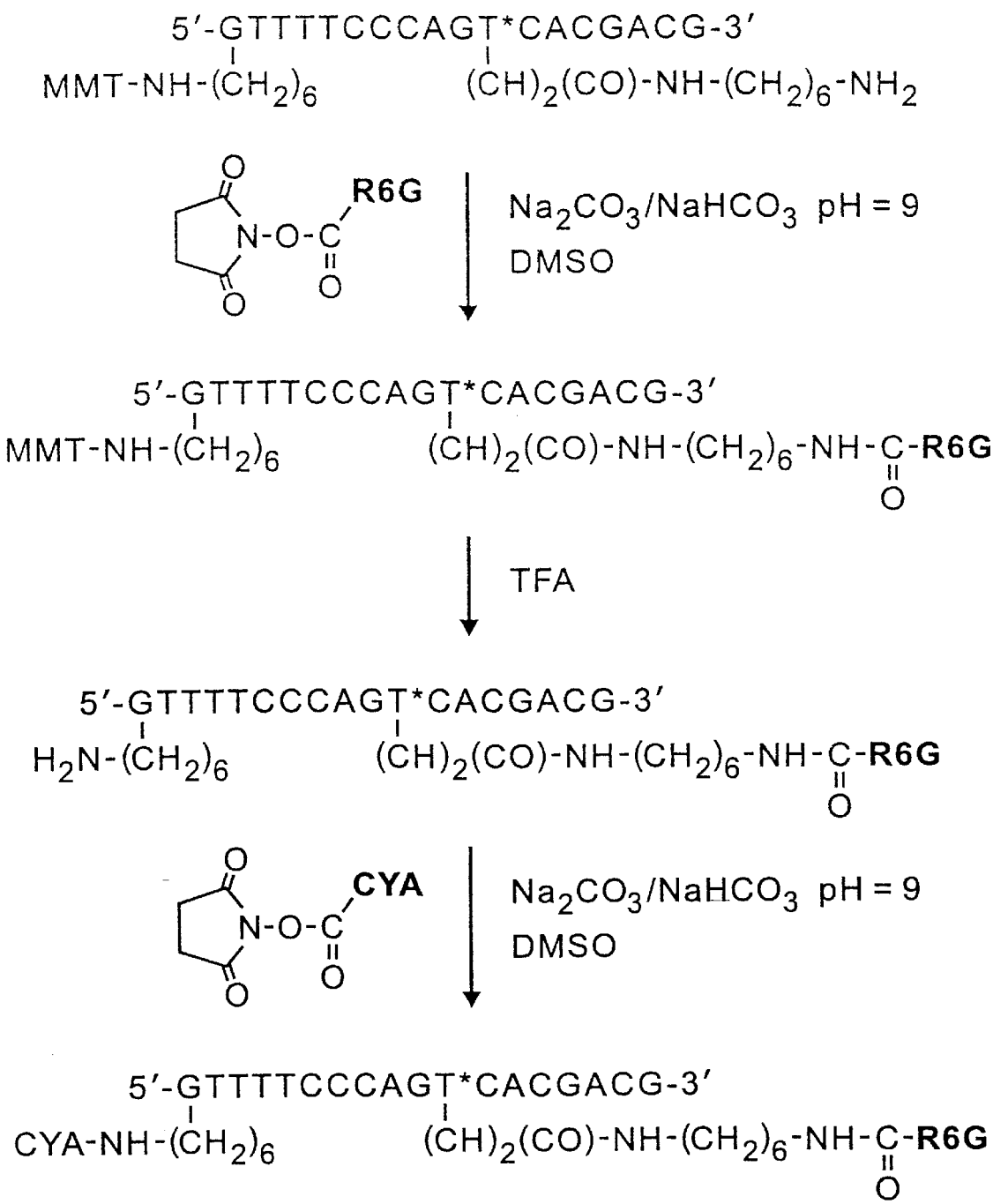
FIG. 2 is an outline of a synthetic scheme for the introduction of acceptor and donor fluorophores to an oligonucleotide chain, forming one of the four primers shown in FIG. 1.
Figure 3C:
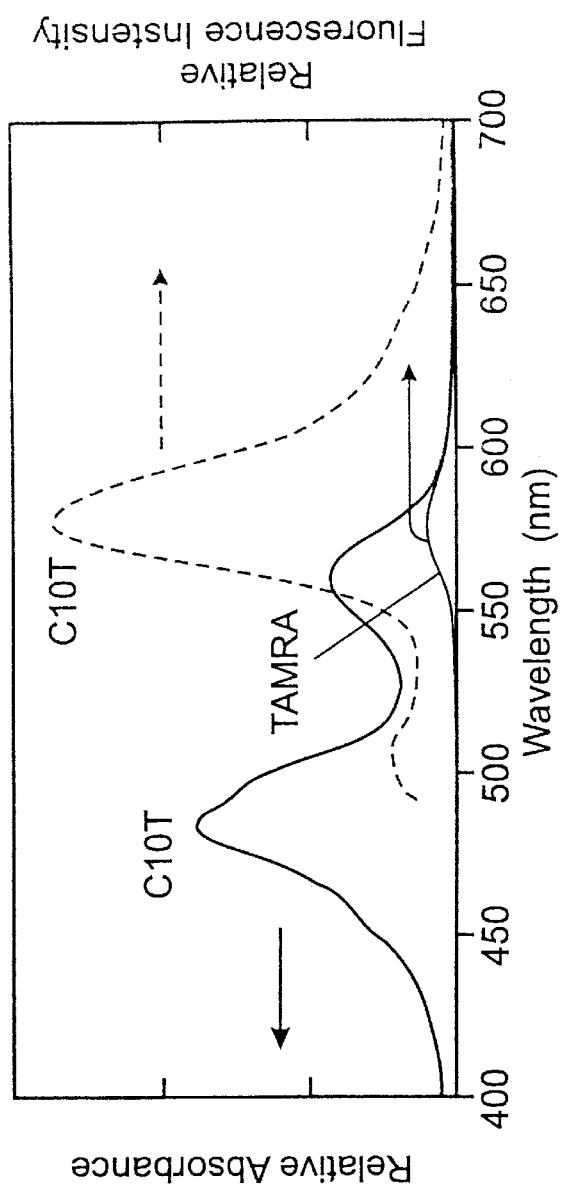
Figure 3D:
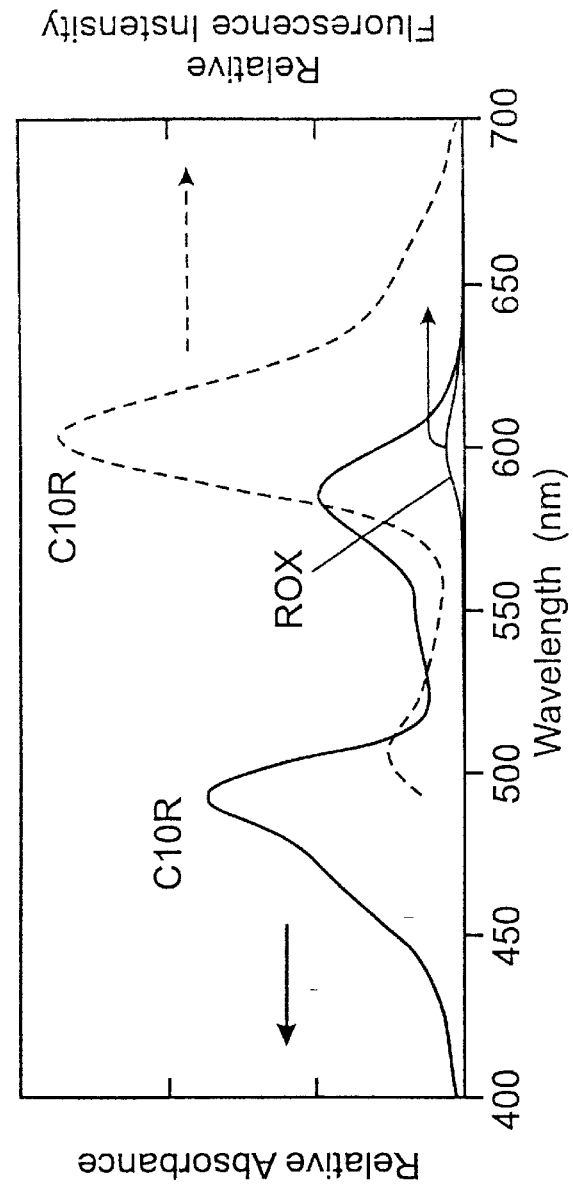

The structures of each of the four primers are shown in FIG. 1, and the reaction scheme for C10R, as one example representing all four primers, is shown in FIG. 2.

The single acceptor dye-labeled precursors and the final ET primers (C10F, C10G, C10T and C10R) were purified as previously described (Ju, J., et al., Proc. Natl. Acad. Sci. USA 92:4347–4351 (1995)). Primers were quantified by their 260 nm absorbance after correction for the contributions to the absorbance from the dyes and then stored in 10 mM Tris-HCl/1 mM EDTA, pH 8.0 at a final concentration of 0.2 pmol/μL. For spectroscopic analysis, primers were dissolved in 1×TBE buffer containing 7 M urea.

DNA Sequencing

Cycle sequencing was performed with M13mp18 DNA template and Thermo Sequenase (Reeve, M. A., et al., Nature 376:796–797 (1995)) and the fragments analyzed on a four-color capillary electrophoresis DNA sequencer. Four reactions were run, one for each dye/ddNTP combination. The reactions containing ddCTP were run with the C10F primer, ddATP with the C10R primer, ddGTP with the C10T primer, and ddTTP with the C10G primer. The following cycle sequencing protocol was used: 0.5 μL of Thermo Sequenase reaction buffer (260 mM Tris/HCl pH 9.5, 65 mM $MgCl_2$) was combined with 1 μL of primer (0.2 pmol), 1 μL of template DNA (0.2 μg) and 3 μL of dNTPs/ddNTP (300:1; dGTP was replaced by DITP) mix. All tubes were preheated at 95° C. for 45–60 seconds, and then 1 μL of a freshly diluted Thermo Sequenase (1.6 units/μL) was added to each tube. Fifteen cycles of 95° C. for 30 seconds, 56° C. for 20 seconds and 72° C. for 2 minutes were carried out on the reaction mixture in a PTC-100 Thermal Cycler (MJ Research Inc., Watertown, Mass., USA). The four reactions were then combined and stopped by adding 15 μL of 7.5 M ammonium acetate and 75 μL of ethanol. After 2 hours at −20° C., the precipitated DNA was collected by centrifugation at 13,100 rpm for 20 minutes and washed twice with 150 μL of ice-cold 70% ethanol. The precipitated DNA was vacuum dried and redissolved in 2 μL of 98% formamide containing 1 mM EDTA. Samples were introduced into a 50-cm long (30 cm effective separation length) 6% T polyacrylamide gel-filled capillary by electrokinetically injecting for 20 seconds. Electrophoresis was performed at 200 V/cm in 1×TBE buffer. A matrix transformation was performed on the raw data to correct for the crosstalk between the four channels to generate the four-color CE sequencing profile.

EXAMPLE 1

This examples illustrates the efficient energy transfer in primers where the donor fluorophore is a cyanine dye in accordance with the present invention.

Four ET primers were synthesized according to the procedures described above: C10F, C10G, C10T, and C10R, using the convention and single-letter symbols indicated above. Additional primers were prepared in parallel-fashion, corresponding to each of the four according to the invention but differing by not including the donor fluorophore, and with the single fluorophore at the 5'-end. Thus, the latter four primers were single-dye labeled primers with the same backbone oligonucleotide and the four acceptor fluorophores as the single dyes, with one exception: the single-dye labeled primer used for comparison to C10G was JOE (J) rather than R6G (G). JOE and R6G have equivalent emission spectra, however, as shown by Hung, S.-C. et al., *Anal. Biochem.* 238:165–179 (1996), the disclosure of which is incorporated herein by reference.

Absorption and emission spectra for the ET primers and the single-dye labeled primers were obtained using equimolar solutions of the primers in 1×TBE containing 7 M urea. The emission spectra were taken with excitation at 488 nm. The results are shown in FIGS. 3a, 3b, 3c, and 3d, where the thick indicate the absorption spectra of the ET primers, the dashed lines the emission spectra of the ET primers, and the thin lines the emission spectra of the single-dye labeled primers.

The absorption spectrum of each primer shows the strong absorption peak of the donor (3-(ε-carboxypentyl)-3'-ethyl-5,5'-dimethyloxacarbocyanine) at 488 nm as well as that of the acceptor. In the case of C10G, the absorption peak of the acceptor occurs at 532 nm due to the R6G in C10G. In the case of C10T, the absorption peak of the acceptor occurs at 560 nm due to the TAMRA. In the case of C10R, the absorption peak of the acceptor occurs at 589 nm due to the ROX.

For the emission spectra, all obtained with excitation at 488 nm, the emission maximum of C10F is at 521 nm, that of C10G is at 555 nm, that of C10T is at 580 nm, and that of C10R is at 605 nm. The location of these maxima (dashed lines) compared to the locations of the maxima obtained with the single-dye labeled primers (continuous thin lines) indicates that the emission spectra are dominated by the acceptor emission in each case. This indicates efficient energy transfer from the donor to the acceptor.

Efficient energy transfer is further confirmed by comparing the heights of the emission maxima for the ET primers (dashed lines) with the heights of the emission maxima for the single-dye labeled primers (continuous thin lines), showing how much of the total emission by the acceptor fluorophore results from energy transfer from the donor: at the same molar concentrations, the intensity at the C10F emission maximum is 1.4 times the intensity of the FAM single-dye labeled primer; the corresponding factor for C10G is 2.7; the corresponding factor for C10T is 17; and the corresponding factor for C10R is 24.

Figure 4:
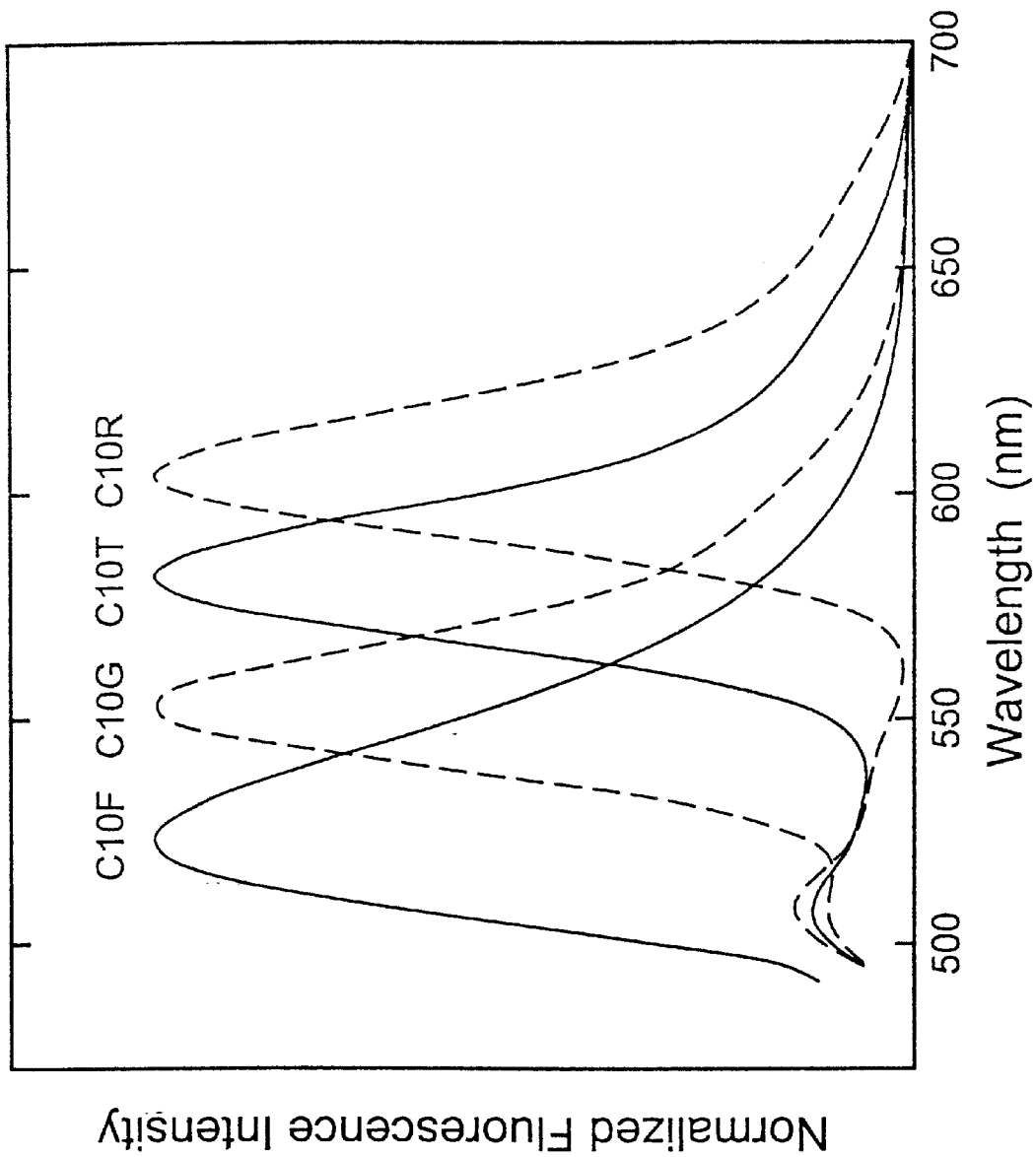
FIG. 4 shows the fluorescence emission spectra of the four labels of FIGS. 3a through 3d, superimposed to show the separation in peak maxima.

FIG. 4 shows the emission spectra for the four ET primers, normalized and superimposed on the same wavelength scale. These spectra show that the residual emission of the common C donor fluorophore is very low, and they also show that there is very little crosstalk between the primers. This contributes materially to the accuracy of base calling. The ET efficiency was calculated to be 90% for C10G, 78% for C10T, and 70% for C10R.

Figure 5D:
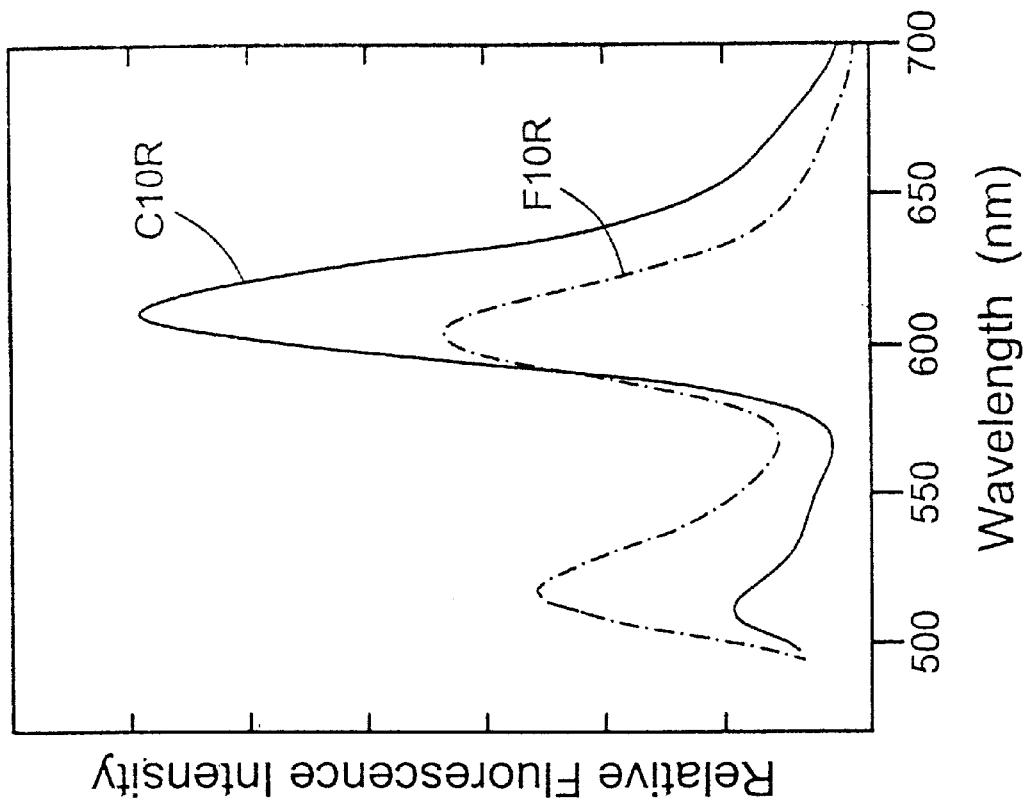
FIG. 5d compares the emission spectra of the same two donor-acceptor labels.
Figure 5C:
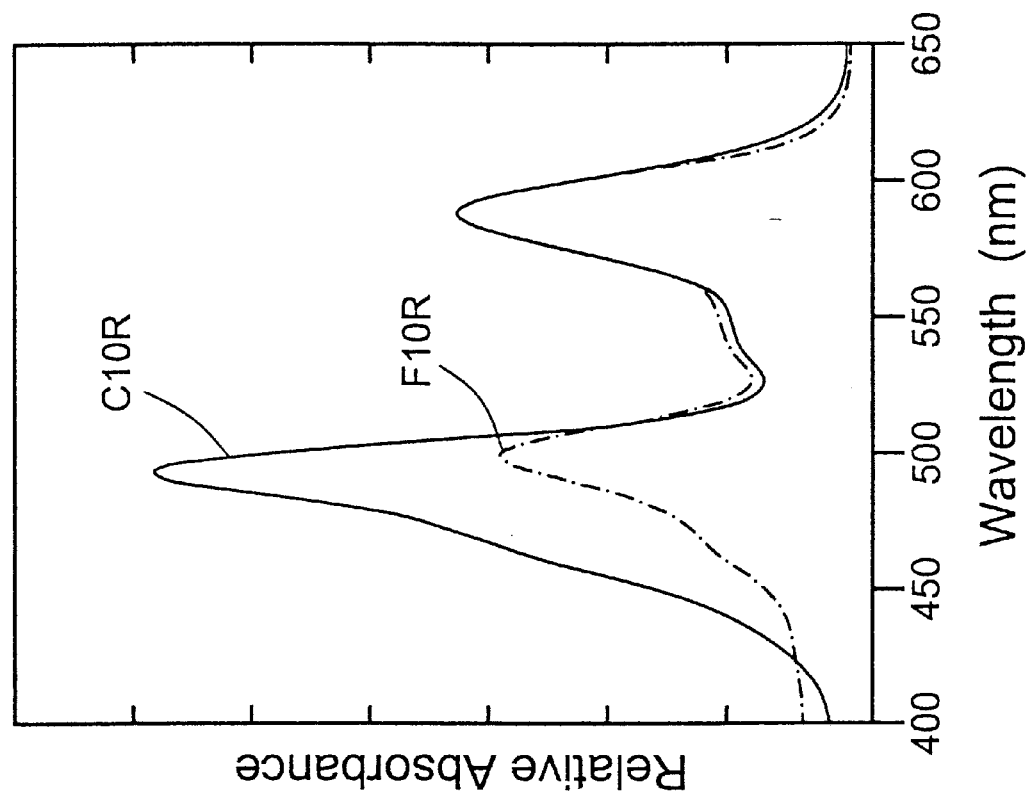
FIG. 5c compares the absorbance spectra of a donor-acceptor label within the present invention with that of a donor-acceptor label of the prior art.

Relative quantum yields are illustrated in FIGS. 5a, 5b, 5c, and 5d. FIGS. 5a and 5b show the absorbance and emission spectra, respectively, of the individual dyes CYA (continuous lines) and FAM (dashed lines). FIG 5a shows that the absorbance of CYA (whose molar extinction coefficient at 488 nm is 142,000 $M^{-1}$ $cm^{-1}$) is about twice that of FAM (whose molar extinction coefficient at 488 nm is 60,000 $M^{-1}$ $cm^{-1}$). FIG. 5b shows that the fluorescence emission of FAM is approximately 5 times that of CYA. Thus, the quantum yield of CYA is approximately 10% that of FAM. FIGS. 5c and 5d show the absorption and emission spectra, respectively, of the ET primers, comparing a primer within the scope of the invention, C10R, with one outside the scope of the invention F10R (in which FAM serves as the donor fluorophore). The donor (488 nm) absorbance of C10R is approximately twice that of F10R, and the fluorescence emission is also approximately twice that of F10R. The observation that the ratio of the maximum absorbance of CYA to that of FAM (FIG. 5a) is the same as the ratio of the fluorescence emission of C10R to that of F10R (FIG. 5d) upon excitation at the maximum absorbance wavelength indicates that the rate of energy transfer ($k_T$) is much higher than the competing rates of fluorescence emission ($k_F$) or radiationless decays ($k_R$) of the CYA singlet state.

EXAMPLE 2

This example shows how the fluorescence emission of energy transfer labels varies with the spacing between the donor and acceptor fluorophores.

Figure 6B:
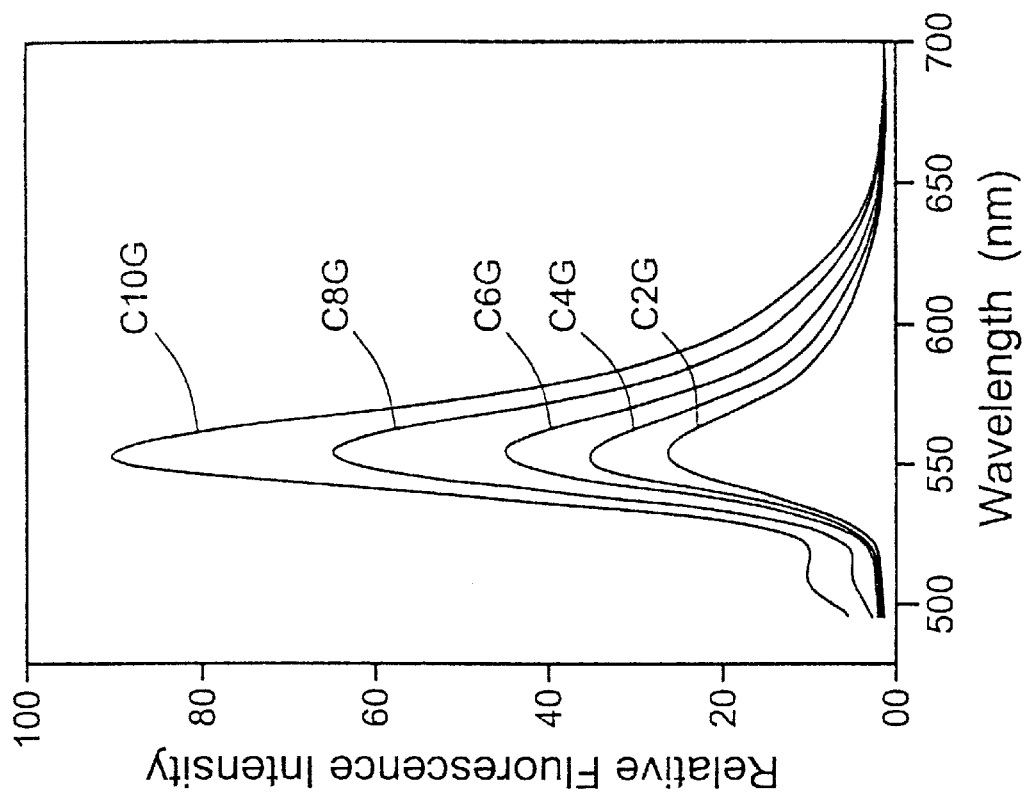
FIGS. 6a, 6b, 6c, and 6d show the emission spectra of four different energy transfer primers, each with five different spacings between the dyes along the oligonucleotide backbone, the five spectra superimposed in each case to show the differences in the fluorescence emission intensity due to variations in the spacing.
Figure 6A:
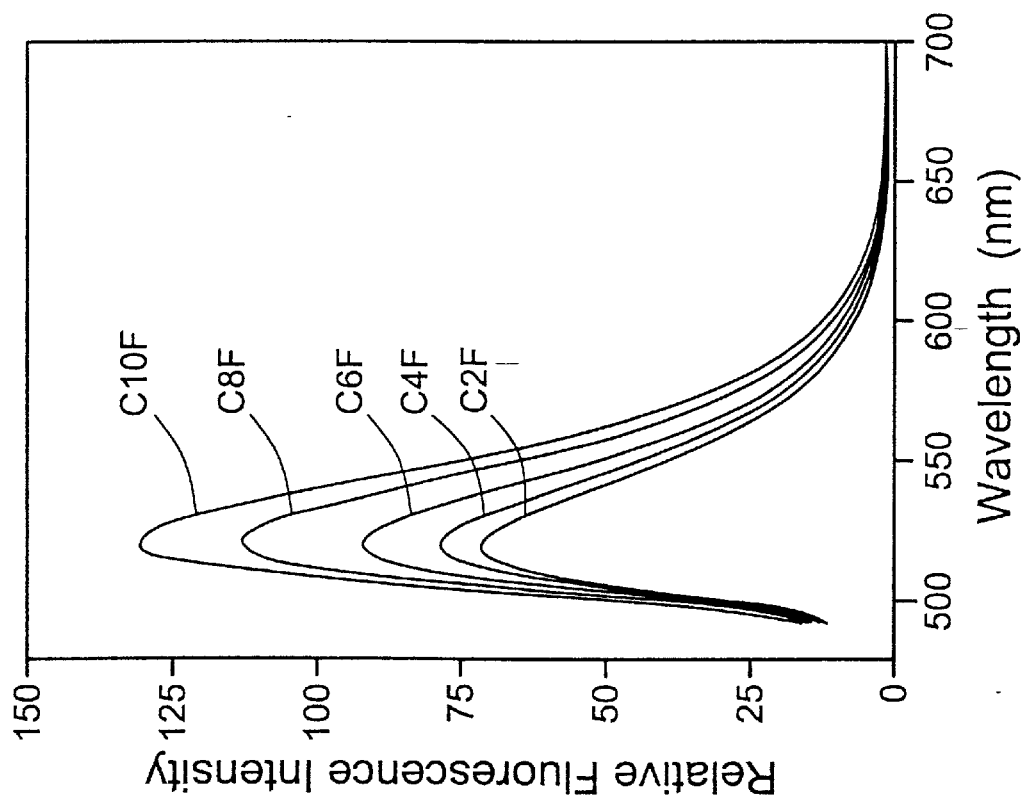
Figure 6D:
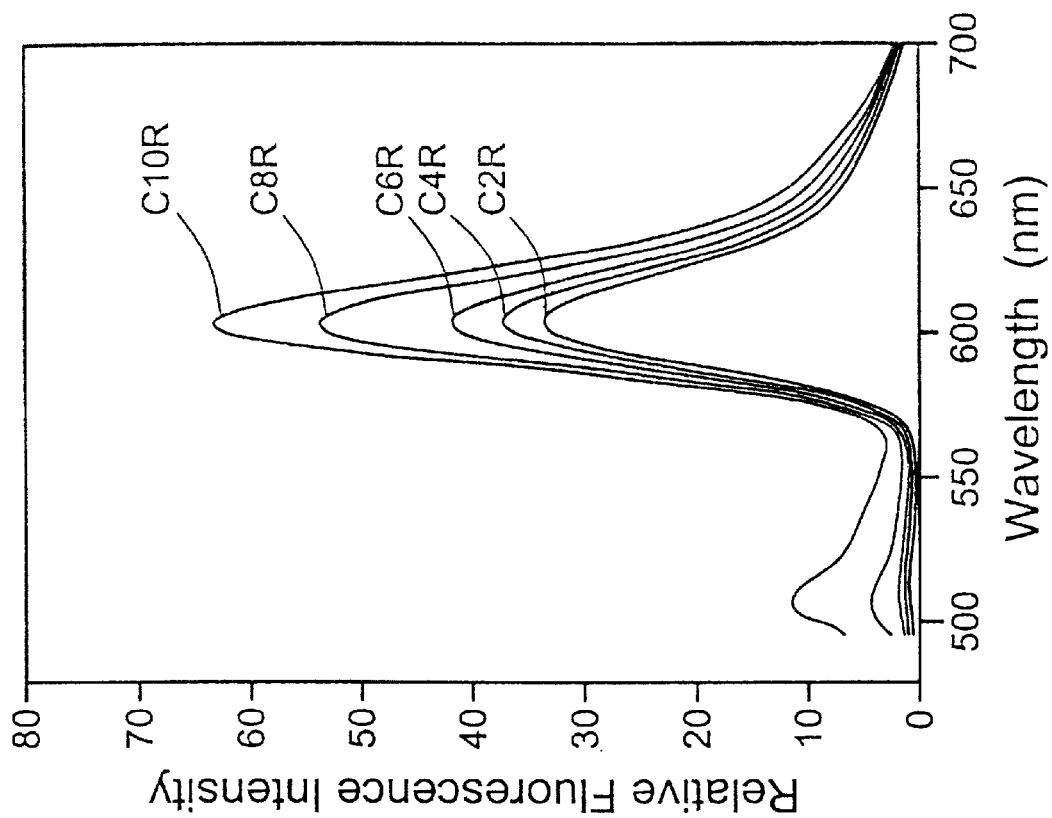
Figure 6C:
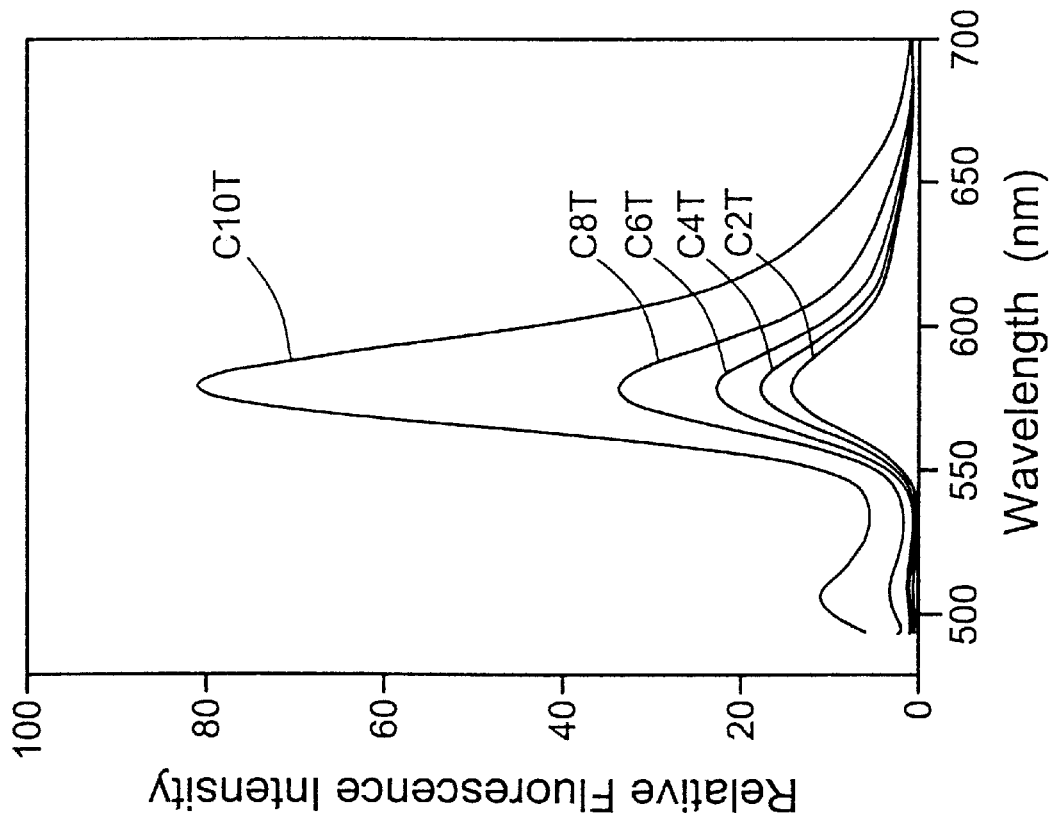

The four donor-acceptor pairs addressed in Example 1 were used, each with five different spacings between donor and acceptor (i.e., spacings of 2, 4, 6, 8, and 10 nucleotides). The emission spectrum for each label was determined at an equimolar concentration in 1×TBE containing 7 M urea with excitation at 488 nm. The results for C2F, C4F, C6F, C8F, and C10F are shown superimposed in FIG. 6a; C2G, C4G, C6G, C8C, and C10G appear in FIG. 6b; C2T, C4T, C6T, C8T, and C10T appear in FIG. 6c; and C2R, C4R, C6R, C8R, and C10R appear in FIG. 6d. These superimposed spectra show that the acceptor fluorescence emission increases as the spacing increases.

For this set of labels when used in situations where the strongest acceptor fluorescence emission is desired, a set with a spacing of 10 nucleotides is optimal. The donor fluorescence emission also varies with spacing, however, but the donor emission with the particular donor used in these labels is absent or insignificant for spacings ranging from 2 to 6 nucleotides. Thus, energy-transfer primers using these fluorophores with nucleotide spacings of 2 to 6 nucleotides are particularly valuable in many DNA fragment studies, where minimization of crosstalk from donor fluorescence emission is particularly valuable.

EXAMPLE 3

This example illustrates a four-label set in which all labels are rhodamines, as opposed to three rhodamines and one fluorescein as in the preceding examples. In many applications of this invention, a close match between the structural characteristics and net charge of all four acceptor fluorophores is desirable because this would minimize any differences between the mobilities of the four set of DNA sequencing fragments obtained by extension of a set of the four ET primers with distinctive emissions.

Figure 7A:
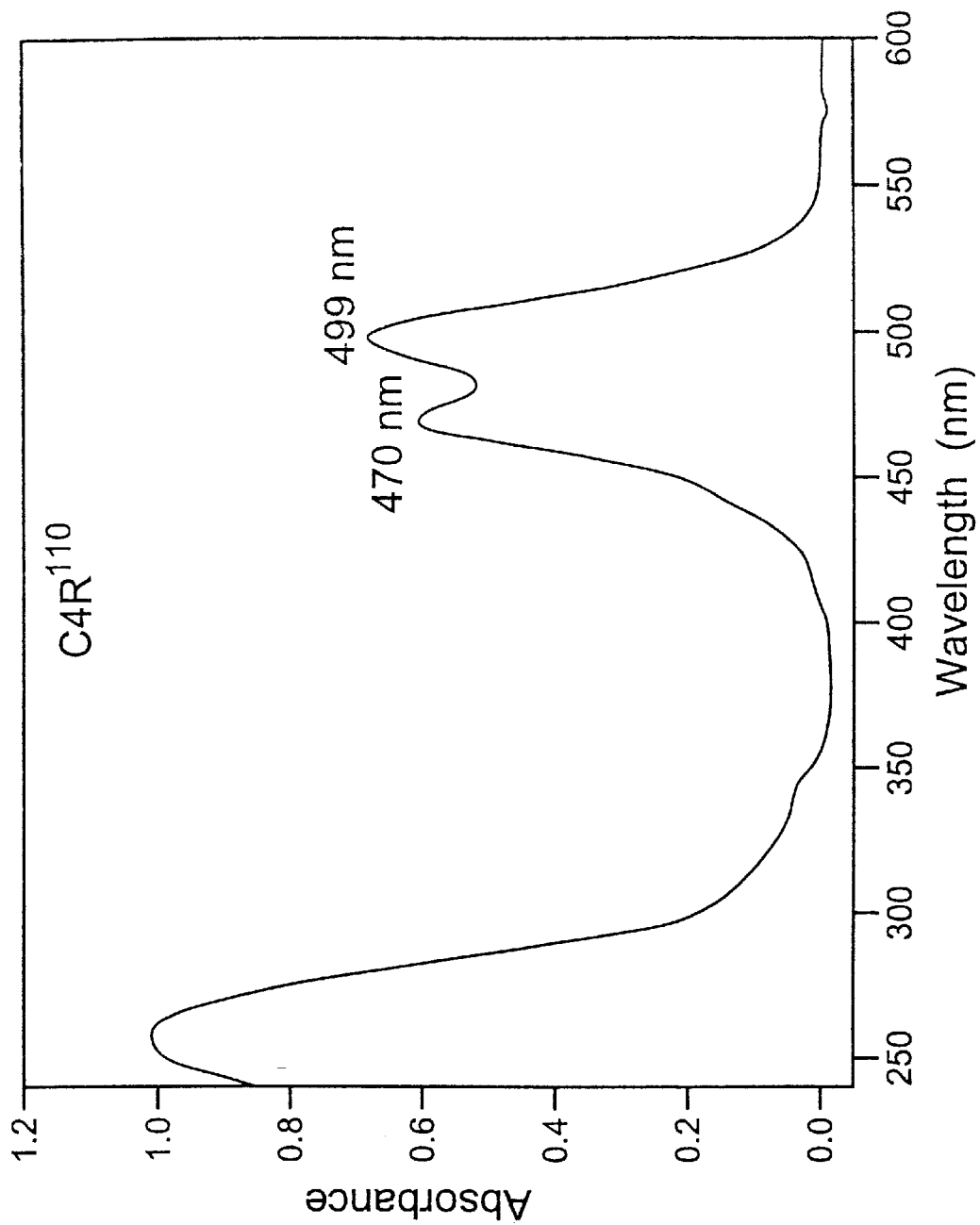
FIG. 7a shows the absorption spectrum of a single energy transfer label within the scope of the invention.

The four primers used in this experiment were the same as the 4-nucleotide spacing primers of the preceding example, except that C4F was replaced with C4R$^{110}$, where R$^{110}$ is 5-(and 6-)carboxyrhodamine 110, whose $\lambda_{max}^{Abs}$=498 nm, $\epsilon_{max}$=78,000 M$^{-1}$ cm$^{-1}$, and $\lambda_{max}^{Em}$=530 nm. The absorption spectrum of C4R$^{110}$ is shown in FIG. 7a, and the normalized superimposed fluorescence emission spectra of the four-primer set are shown in FIG. 7b all measurements determined in 1×TBE containing 7 M urea with excitation at 488 nm.

Figure 7B:
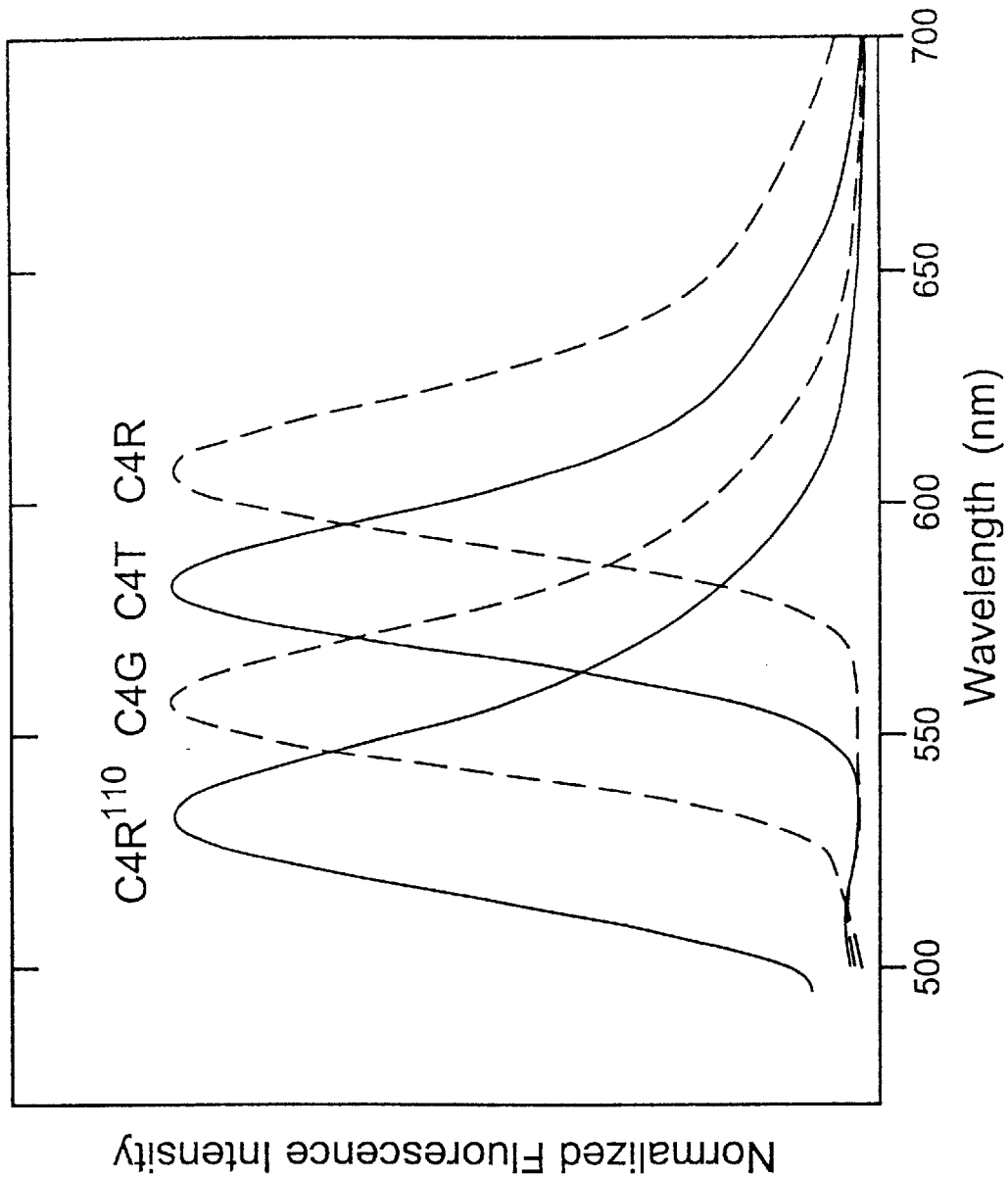
FIG. 7b shows the emission spectrum of this label superimposed over the emission spectra of three other labels in a four-label set.

The superimposed emission spectra of FIG. 7b show excellent separation between the fluorescence emissions of the four primers, which provides for excellent DNA sequencing results.

EXAMPLE 4

This example shows the electrophoretic mobility shifts attributable to the four CYA-containing ET primers prepared in Example 1, and compares them to the electrophoretic mobility shifts of the four prior art ET primers differing from the CYA-containing primers by substituting FAM for the CYA.

Individual primers at concentrations of 1×10$^{-9}$ M each were mixed together in 98% formamide and 1 mM EDTA, and subjected to electrophoresis in a capillary electrophoresis system, using a capillary columns 30 cm in length (20 cm to detection window) and 75 microns in diameter, and a running voltage of 200 V/cm. The column contained 1% linear polyacrylamide prepared in 1×TBE buffer with 7 M urea. Sample injection was achieved by electrokinetic means at 5 kV for 5 seconds. Fluorescence intensities were observed at 525, 550, 580 and >590 nm, and electropherograms were obtained at each wavelength.

Figure 8A:
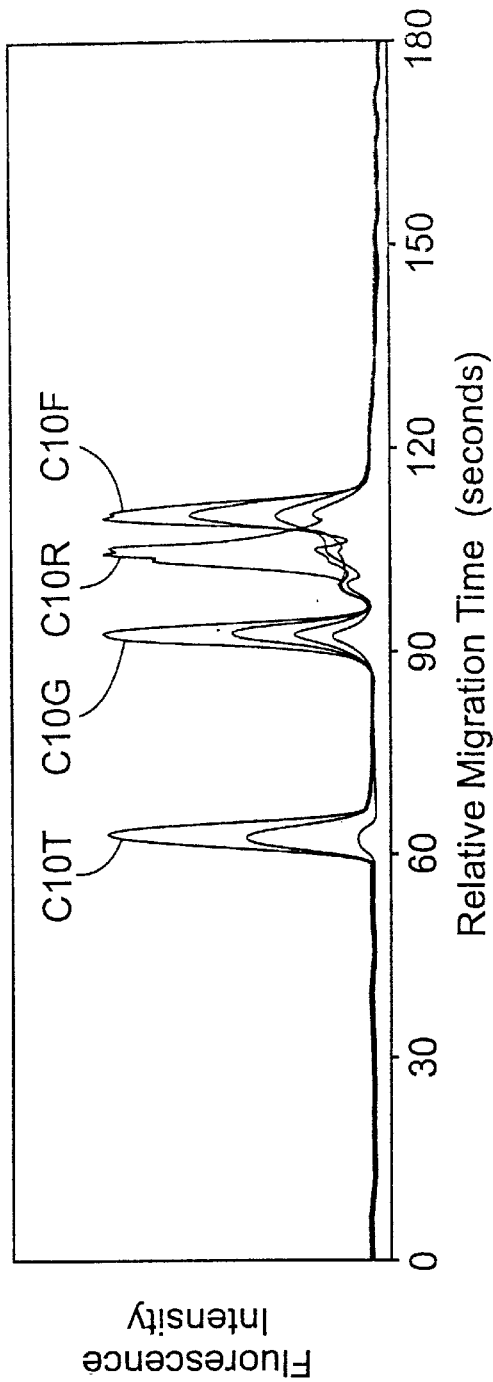
FIG. 8a shows the electrophoretic migration times of the four labels of FIGS. 3a through 3d and 4.

In one experiment, the four CYA-containing primers were used, and the four electropherograms (one at each of the four wavelengths) are shown in FIG. 8a. Since the electropherograms are superimposed, each primer appears as four peaks at the same migration time but at different intensities. The migration time difference between C10T and C10G is 30 second; the migration time difference between C10G and C10R is 12 seconds; and the migration time difference between C10R and C10F is 5 seconds. Thus, the largest relative difference in migration time for these four C10 primers is 47 seconds (C10T to C10F).

Figure 8B:
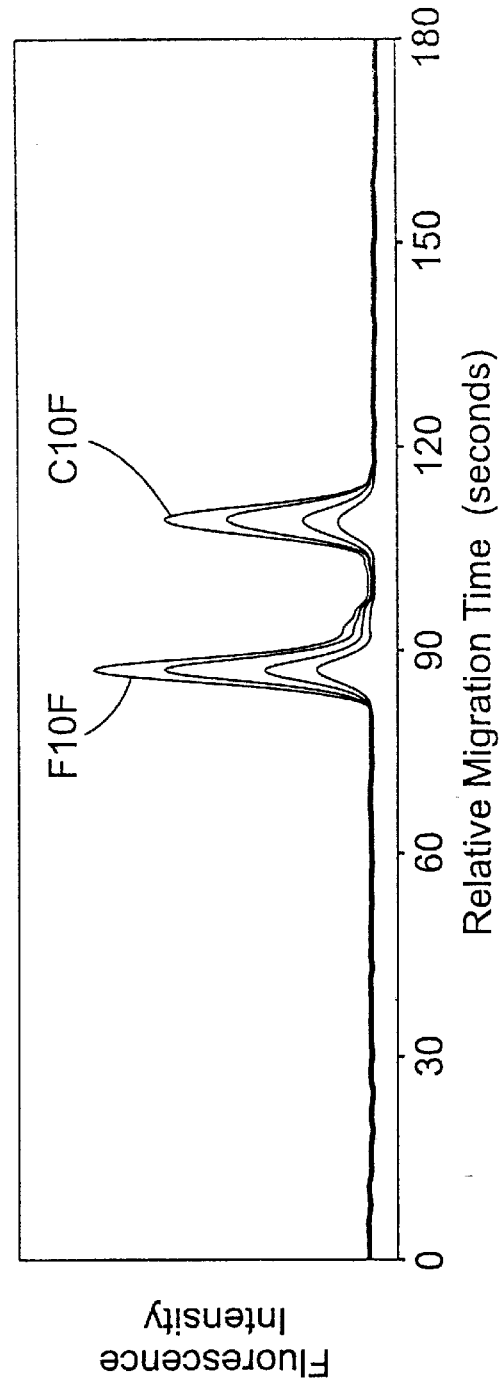
FIGS. 8b, 8c, 8d, and 8e compare the electrophoretic migration times of each of the four labels individually with analogous labels of the prior art that have the same acceptor fluorophores but a different donor fluorophore.
Figure 8C:
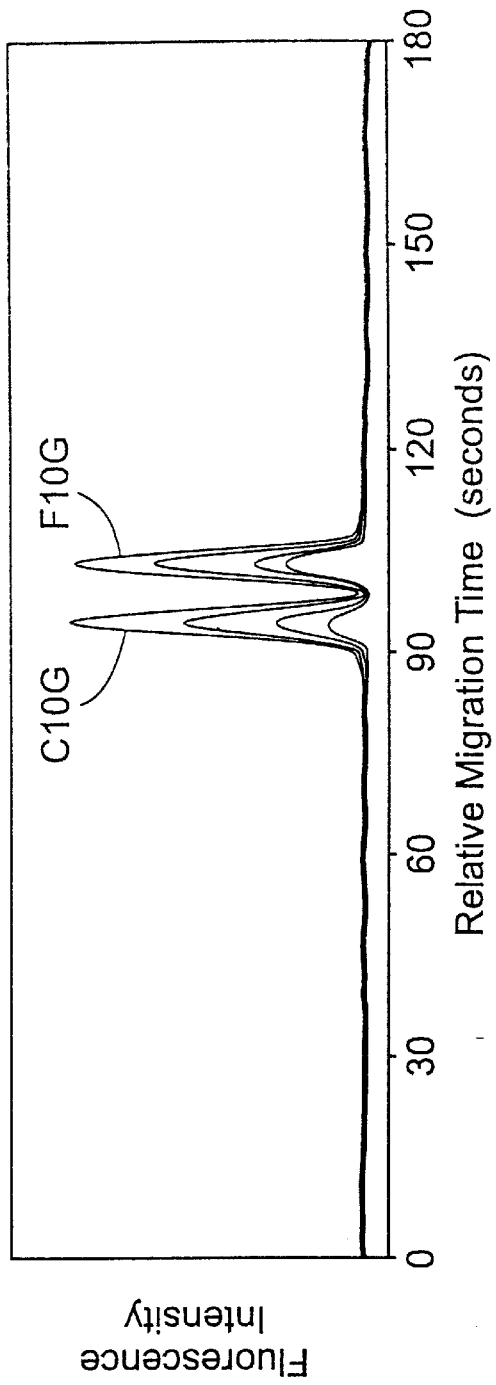
Figure 8D:
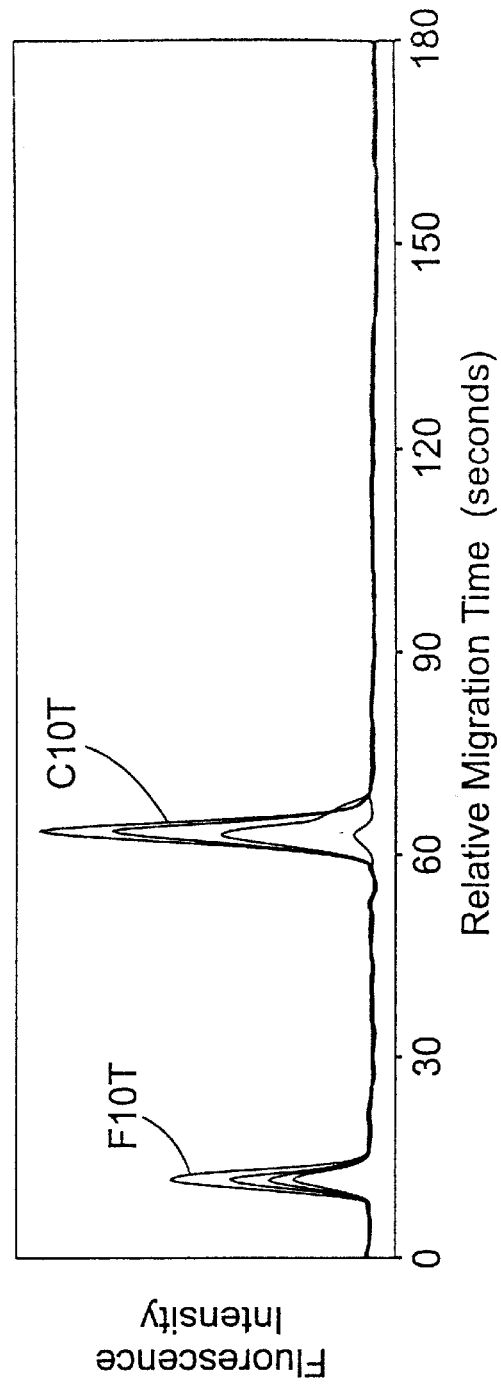

In a second experiment, the C10F primer was used in combination with the F10F primer, and the four electropherograms are shown superimposed in FIG. 8b. The migration time difference is 23 seconds. Similarly, C10G and F10G are compared in FIG. 8c, showing a migration time difference of 9 seconds; C10T and F10T are compared in FIG. 8d with a migration time difference of 52 seconds; and C10R and F10R are compared in FIG. 8e with a migration time difference of 15 seconds. The largest relative difference in migration time for the four F10 primers is 91 seconds, as compared to 47 seconds for the four C10 primers.

Figure 8E:
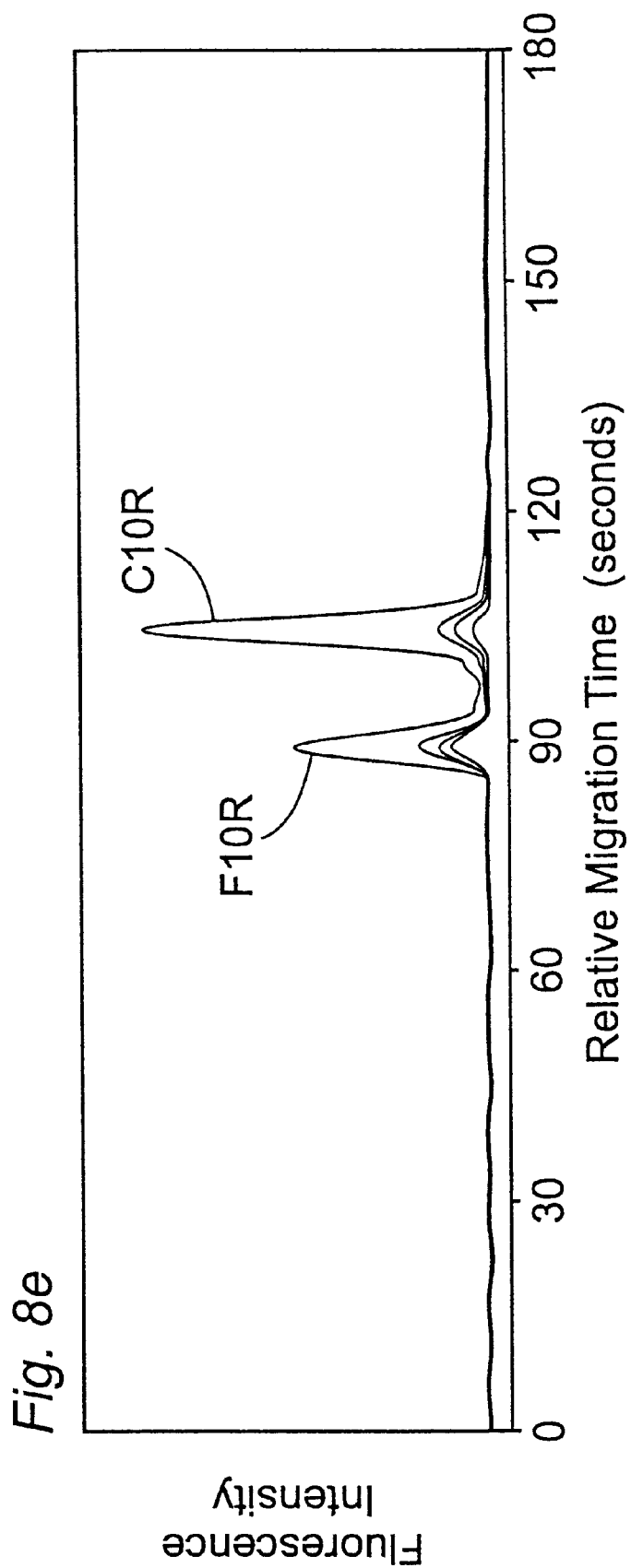

These electropherograms also show the relative fluorescence emission intensities. The signal strength of C10F is 0.8 times that of F10F (FIG. 8b); the signal strength of C10G is equal to that of F10G (FIG. 8c); the signal strength of C10T is 1.7 times that of F10T (FIG. 8d); and the signal strength of C10R is 1.7 times that of F10R (FIG. 8e).

EXAMPLE 5

This example illustrates the use of a four-primer set within the scope of this invention in DNA sequencing. The four primers were those prepared in Example 1—C10F, C10G, C10T and C10R. The DNA sequenced was single-stranded M13mp18.

Cycle sequencing was performed using Thermo Sequenase, with 0.2 pmol primer and 0.2 μg of DNA template for each base extension. The sequencing profile was generated by capillary electrophoresis on 6% T linear polyacrylamide and 1×TBE buffer. The sequence was identified by the color of each peak, with C10F appearing as green, C10G appearing as blue, C10T appearing as black, and C10R appearing as red. The separations extended to 530 bases in 110 minutes with strong signals. Beyond this point, large biased reptations appeared. The raw intensity data were transformed using a crosstalk matrix method. After applying a small mobility correction, a blind manual reading of the resulting sequence produced 500 bases with 100% accuracy relative to the known sequence of M13mp18. When a parallel run was performed with F10F, F10G, F10T and F10R as the primers and the two profiles compared, the fluorescence emission crosstalk between the C10-labeled DNA fragments was less than that seen with the corresponding F10-labeled fragments.

The foregoing is offered primarily for purposes of illustration. It will be readily apparent to those skilled in the art that further modifications, variations and substitutions can be made in the methods, materials, and applications disclosed herein without departing from the spirit and scope of the invention.

We claim:

1. In a method for sequencing a nucleic acid fragment, comprising:
   (i) hybridizing an oligonucleotide primer to said fragment,
   (ii) copying said fragment with a DNA polymerase in separate reaction vessels, each reaction vessel containing dNTPs, one of a set of distinct labeled oligonucleotide primers, all of which bind to a complementary sequence in said fragment, and one of a plurality of dideoxynucleotides, to generate single stranded DNA sequencing fragments, each labeled oligonucleotide primer comprising an oligonucleotide backbone having bonded thereto a donor fluorophore and an acceptor fluorophore in energy transfer relationship, the donor fluorophore of each labeled oligonucleotide primer absorbing light at a wavelength that is substantially common among all labeled oligonucleotide primers and the acceptor fluorophores emitting light energy at wavelengths that differ among labeled oligonucleotide primers in said set, and
   (iii) separating the resulting mixture of single-stranded DNA sequencing fragments into bands and determining the sequence by means of the order of the bands, the improvement in which the donor fluorophore of each labeled oligonucleotide primer is a cyanine dye characterized by a quantum yield of between about 0.01 and about 0.25, and each acceptor fluorophore has a quantum yield of at least 0.3.

2. In a method for the identification and detection of single stranded nucleic acid fragments in a mixture of nucleic acid fragments, said method comprising:
   (i) hybridizing different nucleic acid fragments in said mixture to different probes, each probe comprising an oligonucleotide backbone having bonded thereto a donor fluorophore and an acceptor fluorophore in energy transfer relationship, the donor fluorophore of each labeled oligonucleotide primer absorbing light at a wavelength that is substantially common among all labeled oligonucleotide primers and the acceptor fluorophores emitting light energy at wavelengths that differ among the different probes, (ii) separating said nucleic acid fragments thus hybridized, according to mobilities of said nucleic acid fragments, and (iii) detecting said hybridized nucleic acid fragments thus separated, by irradiation at the absorption wavelength of said donor fluorophores and detection of fluorescence emitted by each of said acceptor fluorophores, the improvement in which the donor fluorophore of each label is a cyanine dye having a quantum yield of between about 0.01 and about 0.25, and each acceptor fluorophore has a quantum yield of at least 0.3.

3. In a method for the identification and detection of single or double stranded nucleic acid fragments in a mixture of nucleic acid fragments, said method comprising:

(i) labeling each nucleic acid fragment of said mixture by means of apolymerase chain reaction employing a primer comprising an oligonucleotide backbone having bonded thereto a donor fluorophore and an acceptor fluorophore in energy transfer relationship, (ii) separating said nucleic acid fragments thus labeled, according to mobilities of said nucleic acid fragments, and (iii) detecting said hybridized nucleic acid fragments thus separated, by irradiation at the absorption wavelength of said donor fluorophore and detection of fluorescence emitted by said acceptor fluorophore, the improvement in which said donor fluorophore is a cyanine dye having a quantum yield of between about 0.01 and about 0.25, and said acceptor fluorophore is a dye has a quantum yield of at least 0.3.

4. In a method for the identification and detection of single stranded nucleic acid fragments in a mixture of nucleic acid fragments, said method comprising:

(i) ligating different nucleic acid fragments in said mixture to different labels, each probe comprising an oligonucleotide backbone having bonded thereto a donor fluorophore and an acceptor fluorophore in energy transfer relationship, the donor fluorophore of each label light at a wavelength that is substantially common among all labels and the acceptor fluorophores emitting light energy at wavelengths that differ among the different labels, (ii) separating said nucleic acid fragments thus ligated, according to mobilities of said nucleic acid fragments, and (iii) detecting said hybridized nucleic acid fragments thus separated, by irradiation at the absorption wavelength of said donor fluorophores and detection of fluorescence emitted by each of said acceptor fluorophores, the improvement in which the donor fluorophore of each label is a cyanine dye having a quantum yield of between about 0.01 and about 0.25, and each acceptor fluorophore has a quantum yield of at least 0.3.

5. A method in accordance with claims 1, 2, 3, or 4 in which said cyanine dye has an absorption maximum in the wavelength range of about 400 to about 900 nm.

6. A method in accordance with claims 1, 2, 3, or 4 in which said cyanine dye has an absorption maximum in the wavelength range of about 400 to about 900 nm, and said acceptor fluorophore has an emission maximum in the wavelength range of about 450 to about 1,000 nm.

7. A method in accordance with claims 1, 2, 3, or 4 in which said cyanine dye has an absorption maximum in the wavelength range of about 480 to about 550 nm.

8. A method in accordance with claims 1, 2, 3, or 4 in which said cyanine dye has an absorption maximum in the wavelength range of about 480 to about 550 nm, and said acceptor fluorophore has an emission maximum in the wavelength range of about 500 to about 700 nm.

9. A method in accordance with claims 1, 2, 3, or 4 in which said cyanine dye has the formula in which:

X is O or S;

Y is O or S;

$R^1$ is a member selected from the group consisting of H, halo, and $C_1$–$C_6$ alkyl;

$R^2$ is a member selected from the group consisting of H, halo, and $C_1$–$C_6$ alkyl;

$R^3$ is $C_1$–$C_6$ alkyl; and m is zero to 3.

10. A method in accordance with claims 1, 2, 3, or 4 in which said cyanine dye has the formula in which:

X is O;

Y is O;

$R^1$ is a member selected from the group consisting of H and $C_1$–$C_3$ alkyl;

$R^2$ is a member selected from the group consisting of H and $C_1$–$C_3$ alkyl;

$R^3$ is $C_1$–$C_3$ alkyl; and m is 1, 2, or 3.

11. A method in accordance with claims 1, 2, 3, or 4 in which said cyanine dye has the formula in which:

X is O;

Y is O;

R¹ is H or methyl;
R² is H or methyl;
R³ is C₁–C₃ alkyl; and
m is 1.

12. A method in accordance with claims 1, 2, 3, or 4 in which said cyanine dye has the formula

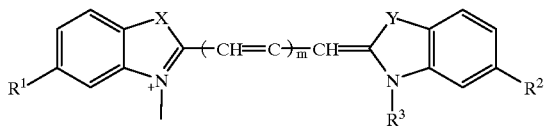

in which:
X is O;
Y is O;
R¹ is H or methyl;
R² is H or methyl;
R³ is ethyl; and
m is 1.

13. A method in accordance with claims 1, 2, 3, or 4 in which said cyanine dye has the formula

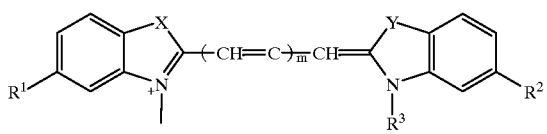

in which:
X is O;
Y is O;
R¹ is methyl;
R² is methyl;
R³ is ethyl; and
m is 1.

14. A method in accordance with claims 1, 2, 3, or 4 in which said donor fluorophore is bonded to the 5' terminal unit of said oligonucleotide backbone.

15. A method in accordance with claims 1, 2, 3, or 4 in which said oligonucleotide backbone is from 5 to 30 nucleotides in length.

16. A method in accordance with claims 1, 2, 3, or 4 in which said oligonucleotide backbone is from 5 to 20 nucleotides in length.

17. A method in accordance with claims 1, 2, 3, or 4 in which said cyanine dye and said acceptor fluorophore are bonded to nucleotides separated by 1 to 29 intervening nucleotides.

18. A method in accordance with claims 1, 2, 3, or 4 in which said cyanine dye and said acceptor fluorophore are bonded to nucleotides separated by 1 to 15 intervening nucleotides.

19. A method in accordance with claims 1, 2, 3, or 4 in which said cyanine dye and said acceptor fluorophore are bonded to nucleotides separated by 4 to 12 intervening nucleotides.

20. A method in accordance with claims 1, 2, 3, or 4 in which said acceptor fluorophore is a xanthene compound.

21. A method in accordance with claims 1, 2, 3, or 4 in which said acceptor fluorophore is a member selected from fluoresceins and rhodamines.

22. A method in accordance with claims 1, 2, 3, or 4 in which said cyanine dye is 3-(ε-carboxypentyl)-3'-ethyl-5,5'-dimethyloxacarbocyanine or 3-(ε-carboxypentyl)-3'-ethyl-oxacarbocyanine, and said acceptor fluorophore is a member selected from the group consisting of fluoresceins and rhodamines.

23. A method in accordance with claims 1, 2, 3, or 4 in which said cyanine dye is 3-(ε-carboxypentyl)-3'-ethyl-5,5'-dimethyloxacarbocyanine or 3-(ε-carboxypentyl)-3'-ethyl-oxacarbocyanine, and said acceptor fluorophore is a member selected from the group consisting of FAM, R6G, TAMRA, ROX, JOE, and rhodamine 110.

24. A method in accordance with claims 1, 2, 3, or 4 in which said cyanine dye is bonded to said backbone by a linking group having the formula

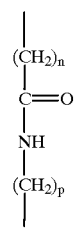

in which n is 1 to 10, and p is 1 to 10.

25. A method in accordance with claims 1, 2, 3, or 4 in which said cyanine dye is bonded to said backbone by a linking group having the formula

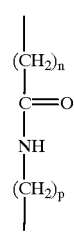

in which n is 1 to 6 and p is 2 to 8.

26. A method in accordance with claims 1, 2, 3, or 4 in which said cyanine dye is bonded to said backbone by a linking group having the formula

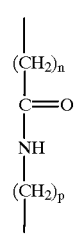

in which n is 4 to 6 and p is 3 to 6.

27. A method in accordance with claims 1, 2, 3, or 4 in which said cyanine dye is bonded to said backbone by a linking group having the formula

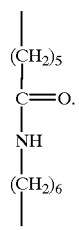
28. A method in accordance with claims 1, 2, 3, or 4 in which said cyanine dye has the formula
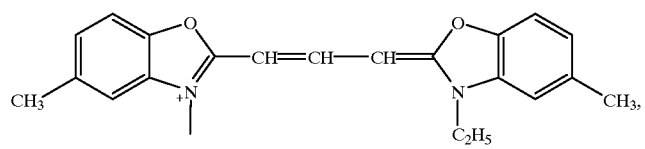
said backbone is an oligonucleotide, and said cyanine dye is bonded to a nucleotide of said backbone by a linking group having the formula
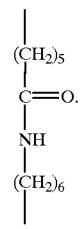

UNITED STATES PATENT AND TRADEMARK OFFICE
CERTIFICATE OF CORRECTION

PATENT NO. : 6,150,107
DATED : November 21, 2000
INVENTOR(S) : Glazer et al.

It is certified that error appears in the above-identified patent and that said Letters Patent is hereby corrected as shown below:

Column 2,
Line 57, delete "teh" and insert therefor -- the --

Column 3,
Line 55, delete "carboxypenyl" and insert therefor -- carboxypentyl --
Line 56, delete "3" and insert therefor -- 3' --

Column 4,
Line 36, delete "rhodamine 110" and insert therefor -- rhodamine 110 (R110) --

Column 10,
Lines 18 and 19, delete "2'-acetaniliodivinyl" and insert therefor
-- 2'-acetanilidovinyl --
Line 33, delete "3'-ethoxacarbocyanine" and insert therefor
-- 3'-ethyloxacarbocyanine --
Line 34, delete gCH2 and insert -- g-CH2 --

Column 11,
Line 19, delete "8.44 (1H, J=13.2" and insert therefor -- 8.44 (1H, t, J-13.2 --
Line 30, delete "of" and insert therefor -- or --
Line 31, delete "carboxypenyl" and insert therefor -- carboxypentyl --
Line 48, delete "(2H, t, J=7.3 Hz, a-CH2(" and insert therefor -- (2H, t, J=7.3 Hz, a-CH2) --

Column 13,
Line 56, delete "rhodamine 110" and insert therefor -- rhodamine 110 (R110) --

Column 17,
Line 6, delete "Fig. 7ball" and insert therefor -- Fig. 7b all --

Signed and Sealed this

Twenty-seventh Day of November, 2001

*Attest:*

NICHOLAS P. GODICI
*Attesting Officer*      Acting Director of the United States Patent and Trademark Office